(12) United States Patent
Ujifusa et al.

(10) Patent No.: US 11,497,526 B2
(45) Date of Patent: Nov. 15, 2022

(54) CERVICAL TENACULUM DEVICE

(71) Applicant: T & J Enterprises, LLC, Lake Stevens, WA (US)

(72) Inventors: Todd Michael Ujifusa, Lake Stevens, WA (US); Marek Andrzej Jaworski, University Place, WA (US)

(*) Notice: Subject to any disclaimer, the term of this patent is extended or adjusted under 35 U.S.C. 154(b) by 437 days.

(21) Appl. No.: 16/685,810

(22) Filed: Nov. 15, 2019

(65) Prior Publication Data
US 2020/0146719 A1 May 14, 2020

Related U.S. Application Data

(63) Continuation-in-part of application No. 16/291,797, filed on Mar. 4, 2019, now Pat. No. 10,512,483.

(60) Provisional application No. 62/760,647, filed on Nov. 13, 2018.

(51) Int. Cl.
*A61B 17/42* (2006.01)
*A61B 17/28* (2006.01)
*A61B 17/29* (2006.01)

(52) U.S. Cl.
CPC .......... *A61B 17/42* (2013.01); *A61B 17/2833* (2013.01); *A61B 2017/2808* (2013.01); *A61B 2017/2905* (2013.01); *A61B 2017/4225* (2013.01)

(58) Field of Classification Search
CPC ............... A61B 17/42; A61B 17/2833; A61B 2017/2808; A61B 2017/2905; A61B 2017/4225; A61B 2017/2924; B25J 1/00; B25J 1/02
See application file for complete search history.

(56) References Cited

U.S. PATENT DOCUMENTS

| | | | | |
|---|---|---|---|---|
| 372,922 A * | 11/1887 | McCord | ............... | A61F 6/146 604/57 |
| 574,943 A * | 1/1897 | Ryman | ............... | A61F 6/146 128/841 |
| 987,173 A * | 3/1911 | Sale | ............... | B25B 9/00 294/100 |
| 2,041,424 A * | 5/1936 | McCormick | ............... | A61F 6/146 128/841 |
| 2,137,710 A * | 11/1938 | Anderson | ............... | A61B 17/2909 606/206 |
| 2,212,013 A * | 8/1940 | Devareaux | ............... | A47J 43/283 294/99.2 |
| 2,232,258 A * | 2/1941 | McCormick | ............... | A61F 6/146 128/841 |
| 2,844,144 A * | 7/1958 | Massey | ............... | A61B 17/42 600/221 |
| 3,945,676 A | 3/1976 | Asamoto | | |
| 4,000,743 A * | 1/1977 | Weaver | ............... | A61B 18/16 606/119 |
| 4,033,618 A * | 7/1977 | Lamb | ............... | B25B 9/00 294/104 |

(Continued)

OTHER PUBLICATIONS

3-Pronged Paris Retriever, Wikipedia, https://en.wikipedia.org/w/index.php?title=3-Pronged_Parts_Retriever&oldid=911160450.

*Primary Examiner* — Phong Son H Dang

(57) ABSTRACT

A surgical device comprising a shaft comprised of a first end and a second end; a clamp configured to be locked or unlocked attached to the first end of the shaft; an actuator shaft that is removably coupled to the shaft and configured to open and close the clamp; and optionally an anchor.

20 Claims, 11 Drawing Sheets

(56) References Cited

U.S. PATENT DOCUMENTS

| | | | | |
|---|---|---|---|---|
| 4,274,415 A * | 6/1981 | Kanamoto | ......... | A61B 17/1227 606/221 |
| 4,444,187 A * | 4/1984 | Perlin | ............... | A61B 17/1227 606/158 |
| 4,575,143 A * | 3/1986 | Nast | ........................ | B25J 1/04 294/24 |
| 5,026,379 A * | 6/1991 | Yoon | ................. | A61B 18/1442 606/151 |
| 5,258,005 A * | 11/1993 | Christian | .............. | A61B 17/29 606/205 |
| 5,382,257 A * | 1/1995 | Lewis | ................ | A61B 17/0401 606/224 |
| 5,407,243 A * | 4/1995 | Riemann | ................ | A61B 17/50 294/100 |
| 5,499,997 A * | 3/1996 | Sharpe | ................. | A61B 17/221 606/205 |
| 5,514,148 A * | 5/1996 | Smith, III | .............. | A61B 17/29 606/151 |
| 5,628,757 A * | 5/1997 | Hasson | ................. | A61B 17/062 606/205 |
| 5,683,405 A * | 11/1997 | Yacoubian | ......... | A61B 17/1227 24/549 |
| 5,730,747 A * | 3/1998 | Ek | ...................... | A61B 17/0487 606/139 |
| 5,749,881 A | 5/1998 | Sackier et al. | | |
| 5,758,420 A * | 6/1998 | Schmidt | ................. | B21F 45/16 72/130 |
| 5,772,597 A | 6/1998 | Goldberger et al. | | |
| 5,826,928 A * | 10/1998 | Shang | .................... | B25B 11/002 294/100 |
| 5,947,982 A * | 9/1999 | Duran | ................. | A61B 17/0625 606/139 |
| 5,954,057 A * | 9/1999 | Li | ........................ | A61B 17/062 606/139 |
| 6,315,340 B1 * | 11/2001 | Chen | ........................ | E01H 1/12 294/100 |
| 6,391,035 B1 * | 5/2002 | Appleby | ............... | A61B 17/128 606/142 |
| 6,402,765 B1 * | 6/2002 | Monassevitch | ...... | A61B 17/064 606/151 |
| 6,984,237 B2 * | 1/2006 | Hatch | ................ | A61B 17/0469 606/144 |
| 6,991,634 B2 * | 1/2006 | Sugiyama | ............ | A61B 17/122 606/151 |
| 7,137,988 B2 * | 11/2006 | Frye | ...................... | A61B 17/062 606/147 |
| 7,211,089 B2 | 5/2007 | Kear et al. | | |
| 8,052,700 B2 * | 11/2011 | Dunn | ................. | A61B 17/1227 606/157 |
| 8,057,490 B2 | 11/2011 | Harris et al. | | |
| 8,066,722 B2 * | 11/2011 | Miyagi | .............. | A61B 17/1285 606/142 |
| 8,092,489 B2 | 1/2012 | Ewers et al. | | |
| 8,104,806 B1 * | 1/2012 | Shih | ........................ | B25J 1/02 294/120 |
| 8,852,088 B2 | 10/2014 | Ransden et al. | | |
| 8,864,776 B2 * | 10/2014 | Bogart | ............. | A61B 17/06004 606/228 |
| 8,968,340 B2 * | 3/2015 | Chowaniec | ........ | A61B 17/0625 606/144 |
| 8,979,872 B2 | 3/2015 | Harris et al. | | |
| 8,986,326 B2 | 3/2015 | Satake et al. | | |
| D725,265 S | 5/2015 | John et al. | | |
| 9,085,085 B2 | 7/2015 | Danitz et al. | | |
| 9,289,216 B2 * | 3/2016 | Weisshaupt | ........ | A61B 17/1227 |
| 9,393,023 B2 * | 7/2016 | Privitera | ........... | A61B 17/122 |
| 9,402,757 B2 * | 8/2016 | Kassab | ................ | A61F 5/0086 |
| 9,492,163 B2 | 11/2016 | Bagaoisan et al. | | |
| 9,572,579 B2 * | 2/2017 | Weisshaupt | ........ | A61B 17/1227 |
| 9,844,389 B2 | 12/2017 | Van Andel | | |
| 9,974,532 B2 | 5/2018 | Baas et al. | | |
| D835,270 S * | 12/2018 | Benson | ........................ | D24/133 |
| D837,982 S | 1/2019 | Adler | | |
| 10,335,178 B2 | 7/2019 | Taylor et al. | | |
| 10,390,851 B2 | 8/2019 | Chu | | |
| 10,570,596 B1 * | 2/2020 | Schneck | ................... | E03C 1/26 |
| 2002/0032454 A1 * | 3/2002 | Durgin | ................. | A61B 17/122 606/151 |
| 2002/0062130 A1 * | 5/2002 | Jugenheimer | ....... | A61B 17/1285 606/142 |
| 2002/0133170 A1 * | 9/2002 | Tsuruta | ................ | A61B 17/221 606/127 |
| 2002/0177859 A1 * | 11/2002 | Monassevitch | ...... | A61B 17/128 606/139 |
| 2003/0069592 A1 * | 4/2003 | Adams | ............... | A61B 17/1227 606/142 |
| 2003/0105488 A1 * | 6/2003 | Chu | ...................... | A61B 17/29 606/205 |
| 2003/0120306 A1 * | 6/2003 | Burbank | ............. | A61L 24/0042 606/205 |
| 2004/0092979 A1 * | 5/2004 | Burbank | ............. | A61B 17/122 606/158 |
| 2004/0097962 A1 * | 5/2004 | Burbank | ............. | A61B 17/1285 606/119 |
| 2004/0153105 A1 * | 8/2004 | Burbank | ................ | A61B 17/42 606/157 |
| 2004/0236349 A1 * | 11/2004 | Gellman | ................ | A61B 17/42 606/119 |
| 2005/0251183 A1 * | 11/2005 | Buckman | ............. | A61B 17/083 606/157 |
| 2005/0277959 A1 * | 12/2005 | Cosgrove | ........... | A61B 17/1285 606/151 |
| 2006/0259076 A1 * | 11/2006 | Burkhart | .................. | A61L 17/04 606/228 |
| 2007/0106314 A1 * | 5/2007 | Dunn | ................. | A61B 17/1128 606/157 |
| 2007/0135843 A1 * | 6/2007 | Burkhart | .................. | D04C 1/12 606/232 |
| 2007/0142860 A1 * | 6/2007 | Kotmel | ................. | A61B 17/42 606/205 |
| 2008/0004659 A1 * | 1/2008 | Burkhart | ............ | A61B 17/0401 606/232 |
| 2008/0315605 A1 * | 12/2008 | Shih | ........................ | B25J 1/02 56/332 |
| 2009/0012545 A1 * | 1/2009 | Williamson, IV | .......................... A61B 17/1285 606/157 |
| 2009/0105720 A1 * | 4/2009 | Boone | .................... | A61B 17/42 606/119 |
| 2009/0318914 A1 * | 12/2009 | Utley | ..................... | A61B 46/13 606/33 |
| 2009/0318965 A1 * | 12/2009 | Burkhart | ............. | A61B 17/0483 606/232 |
| 2010/0010511 A1 * | 1/2010 | Harris | ..................... | A61B 17/29 606/143 |
| 2010/0076344 A1 * | 3/2010 | Kecman | ............... | A61B 1/32 600/220 |
| 2011/0046437 A1 * | 2/2011 | Kassab | ................ | A61F 5/0013 606/157 |
| 2011/0079226 A1 * | 4/2011 | Sakhel | ................ | A61B 17/4241 128/830 |
| 2012/0035631 A1 * | 2/2012 | Hughett, Sr. | ....... | A61B 17/1285 606/157 |
| 2012/0109147 A1 * | 5/2012 | Auerbach | ........... | A61B 17/4241 606/119 |
| 2012/0123445 A1 * | 5/2012 | Hughett, Sr. | ....... | A61B 17/1227 24/485 |
| 2012/0165868 A1 * | 6/2012 | Burkhart | ............. | A61B 17/0401 606/232 |
| 2013/0079810 A1 * | 3/2013 | Isenberg | ............. | A61B 18/1447 606/205 |
| 2013/0172682 A1 * | 7/2013 | Ransden | ............. | A61B 17/0218 600/204 |
| 2013/0345747 A1 * | 12/2013 | Dreyfuss | ............. | A61B 17/0401 606/232 |
| 2015/0190157 A1 * | 7/2015 | Chu | .................... | A61B 17/221 606/127 |

(56) References Cited

U.S. PATENT DOCUMENTS

| | | | |
|---|---|---|---|
| 2016/0166270 A1* | 6/2016 | Hera | A61B 17/221 |
| | | | 606/127 |
| 2016/0220347 A1* | 8/2016 | Hoover | A61F 2/0811 |
| 2016/0331408 A1* | 11/2016 | Benson | A61B 17/4241 |
| 2017/0189007 A1* | 7/2017 | Burkhart | A61F 2/0811 |
| 2019/0105046 A1* | 4/2019 | Jagelski | A61B 17/0057 |

* cited by examiner

CERVICAL TENACULUM DEVICE

PRIORITY CLAIM

This application claims priority to and/or the benefit of U.S. Provisional Patent Application Ser. No. 62/760,647 filed Nov. 13, 2018 and U.S. Non-Provisional patent application Ser. No. 16/291,797 filed Mar. 4, 2019. The foregoing applications are incorporated by reference in their entirety as if fully set forth herein.

BACKGROUND OF THE INVENTION

This invention relates generally to a medical device, and more specifically, to a surgical tenaculum.

BRIEF SUMMARY

This invention relates generally to a medical device, and more specifically, to a surgical tenaculum. Specific details of certain embodiments of the invention are set forth in the following description and in the figures to provide a thorough understanding of such embodiments. The present invention may have additional embodiments, may be practiced without one or more of the details described for any particular described embodiment, or may have any detail described for one particular embodiment practiced with any other detail described for another embodiment.

The surgical tenaculum is a medical instrument used for a variety of purposes, but among its most common is the manipulation of a patient's cervix and uterus during medical procedures, including, but not limited to Dilation & Curettage, Endometrial Biopsy, Abortion, Hysteroscopy, Operative Hysteroscopy, Endometrial Ablation, LEEP/LLETZ Procedure, Colposcopy, Intrauterine Insemination Procedure, Intrauterine Device Insertion, Saline Infusion Sonography, Hysterosalpingogram, and Hysterectomy. During many of the above procedures manipulation of the cervix is key because they typically involve pushing an object through the cervix and into the uterus, and thus require counter-traction be applied to the cervix. Alternatively, in some procedures the tenaculum is used to straighten the patient's uterus to allow the physician access. In simplest terms, the cervix must be grasped, held in place, and pulled towards the practitioner to allow the procedure to move forward.

Typically, during a surgical procedure or when the practitioner requires access to the cervix or uterus, the instruments, including the tenaculum, are inserted into the vagina or other body cavity through a speculum. During the procedure other tools are often inserted into the speculum including, but not limited to, a clamp, catheters, cannula, biopsy devices, diagnostic camera and imaging tools, light sources, and/or irrigation tubes which can further obstruct the practitioner's view of the cervix. In addition, the number of tools that require they be actively held can result in the practitioner, any aides, or even the patient being required to hold a large number of items at once, which can limit the effectiveness of the practitioner. Among many benefits, the present invention allows the necessary, adjustable counter-traction to be placed on the cervix by allowing the tenaculum to attach to a speculum or other stationary component, including possibly the patient's skin, or a strap or harness, thereby potentially freeing a hand of practitioner.

In some embodiments, the surgical device comprises a shaft comprised of a first end and a second end; a clamp configured to be locked or unlocked attached to the first end; an actuator shaft that is removably coupled to the shaft, slidable along the shaft, and configured to open and close the clamp.

BRIEF DESCRIPTION OF THE DRAWINGS

Embodiments of the present invention are described in detail below with reference to the following drawings.

DETAILED DESCRIPTION

Figure 1:
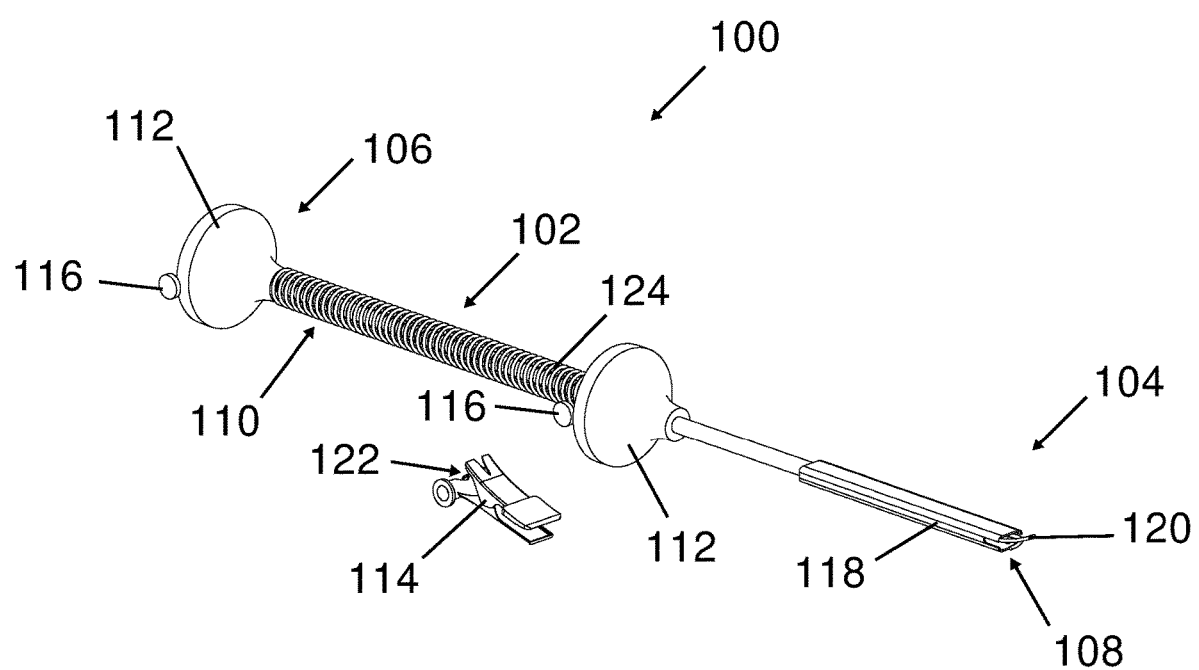
FIG. 1 is a perspective view of a cervical tenaculum device and anchor, in accordance with an embodiment of the invention.

This invention relates generally to a medical device, and more specifically, to a surgical tenaculum. Specific details of certain embodiments of the invention are set forth in the following description and in FIGS. 1-11 to provide a thorough understanding of such embodiments. The present invention may have additional embodiments, may be practiced without one or more of the details described for any particular described embodiment, or may have any detail described for one particular embodiment practiced with any other detail described for another embodiment.

As used herein and unless otherwise indicated, the terms "a" and "an" are taken to mean "one", "at least one" or "one or more". Unless otherwise required by context, singular terms used herein shall include pluralities and plural terms shall include the singular.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

In some embodiments, the invention comprises a shaft comprised of a first end and a second end; a clamp configured to be locked or unlocked attached to the first end of the shaft; an actuator shaft that is removably coupled to the shaft, slidable along the shaft, and configured to open and close the clamp. In some embodiments, the invention has two or more handles that can be attached along the length of the actuator shaft or shaft; in some of these embodiments the portion of the actuator shaft that is between the two handles may be comprised of a coil such that when the two handles are pulled towards each other the interior shaft (or just the shaft) is pressed forward, which operates the clamp such as by opening it or altering its configuration.

In some embodiments the shaft mechanism is further comprised of an actuator shaft that may be operated by a twisting movement, push-pull movement, plunger, quick-release screw, or other means of engaging the actuator and in turn the clamp. In some embodiments the shaft may have multiple components allowing it to be held in various configurations such as being configured to remove the shaft or portions thereof once the clamp is in place, remove the shaft entirely once the clamp is in place, or leave the entire device in the patient.

In some embodiments, the device is comprised of an internal shaft with at least two ends. At one end the clamp may be attached. An external shaft, the actuator shaft, may envelop the internal shaft such; in which case it may be a hollow cylindrical shape so that it wraps around the internal shaft. The interior or actuator shafts may be at least partially flexible and/or compressible; in some embodiments the actuator shaft may be further comprised of a removably attached coil of material such as, but not limited to, metal or a polymer that may partially envelop the rest of the actuator shaft. In some embodiments, there may be two handles attached at either end of the actuator shaft in order to attach it to the internal shaft; and in some of those embodiments the handles may be attached by screwing onto the internal shaft to keep the external actuator shaft in place, or may be attached by a set-screw, clasp, or clamp; in some embodiments the actuator shaft or a portion thereof may be trapped between them or held via pressure from set screws against the interior shaft. In some embodiments the clamp is expressed and opened by pressing on the rear handle so that the actuator shaft compresses and in turn pushes the internal shaft forward.

In some embodiments the internal and actuator shafts may be flexible such that they can be bent, allowing a practitioner to attach them to an anchor or other grounding point while also moving them out of the way so that the practitioner can work. In some embodiments, the device may have specific points along the internal and actuator shafts where the bending occurs, while in other embodiments the full length of the shaft component may be flexible. The internal or actuator shafts may have threading in some embodiments that is configured to receive one or more handles; in other embodiments the handles attach via set-screws that place press the handle into the shaft. The shafts may be substantially cylindrical, flat, or other shapes. In at least one embodiment the shafts are substantially cylindrical and the interior shaft is able to rotate within the actuator shaft though in various embodiments there may be pressures preventing free rotation such as pressure applying the handle to the shaft via the set screw, or a close fit from the actuator shaft. In some embodiments the shafts are substantially straight, while in others one or both shafts may be curved or bent to enable specialized manipulation of tissue or articles.

In some embodiments, a practitioner or user engages the device by pressing on the actuator shaft while pulling back on the shaft or a handle on the shaft, which in turn causes the clamp to open. Some examples involve a sheath overlapping the clamp that fully covers it when the actuator is not being utilized, but when a user presses the handles together it pushes the clamp out of the sheath which allows the clamp to open; in such embodiments it may favor an opened position instead of closed or may even be a single piece of material which was constructed in an open position. The tips of the clamp can then be applied to a cervix or other article to be held, and once it is in a location the practitioner deems appropriate the actuator shaft and handle can be released, which relieves the pressure keeping the clamp open and closes the clamp, thereby taking hold of the article. The device is then free to remain in the patient and grasping the article while the practitioner works utilizing other tools.

In some embodiments the clamp is a jawed-clamp or other configuration wherein the clamp may automatically favor a closed position over an open one and exerts tension on the points or pressure exerting areas of the clamp's tip. Some examples may have a complex clamp structure wherein the clamp has multiple modes that can be operated through the actuator shaft and/or handles; such as locking the clamp in its current position by twisting a handle at a certain point, or it may have a click-in mechanism allowing it to hold pressure that can be quickly released. In some embodiments, the clamp has a mechanism such as a screw, ratchet, or other variable tension means to place tension on the grasping means. In some embodiments the clamp may be constructed as a single component wherein a piece of material, possibly a metal, is split and forked so that two tines are created, then bent towards each other, leaving a gap between them as necessary for the user, such that when the tines are pressed towards each other the tips close the gap. In some embodiments, the tips may contact each other, while in other embodiments they may overlap or pass each other. In some embodiments the mechanism is in the form of pointed tips such as found in a common surgical tenaculum, while in other embodiments it may involve a shaped pad or rod allowing it to displace the force over the surface it is grasping and diminish any trauma to the area or article being grasped. In some embodiments the clamp may be a tether that encircles the area to be held like a noose or similar means. In some embodiments the clamp is a pinch-based grasping means with two prongs, while in others it may have additional prongs as needed to sufficiently grasp and hold the article in question. In some embodiments, the clamp is comprised of one or more hinges pivoted together such that when tension is placed on corresponding ends of the hinges the opposite ends are closed. In some embodiments, the clamp is comprised of one or more hinges, such as scissor-hinges, that are connected with each other and operable against each other such that operating one hinge will operate another. In some embodiments the clamp may be locked into position such that it does not exert any additional pressure once they are locked or closed to a certain degree; in other embodiments they may exert continuous closing or opening pressure. In some embodiments the clamp may be at least partially flexible.

In some embodiments, the clamp does not automatically favor a closed position but may favor a neutral or open position. Examples of such may feature a clamp that is comprised of a single piece of material or it may have a spring integrated into the jaws of the clamp that pushes it open. In some embodiments, the clamp is also a scissors-style hinge mechanism wherein a distal end is designed to be a grasping end while a proximal end is the end engaged by the actuator. In some embodiments, the clamp may have a quick-release mechanism, retrieval cord, or other means of disengaging tension. In some embodiments, the scissors-style hinge clamp may have a means of disengaging tension including a latch, catch, screw, and/or may be pushed on by the tether in order to release the tension.

In some embodiments the device further comprises a tether that may be attached along the length of the device. In some embodiments this tether is comprised of silicone or another substance from the list including, but not limited to, silicone, rubber or plastic. In some embodiments, the tether is a chain made of one or more substances from the list including, but not limited to, metal or plastic. In some embodiments, the tether can be pulled to place tension on the clamp and allow a user to in turn place tension on the article which the clamp is grasping, such as, but not limited to, in the case of gynecological procedures, a cervix. In some embodiments the clamp is attached to the tether by a variable tension means such as, but not limited to, a spring. In some embodiments, the tether is comprised of a chain from the list including, but not limited to, a box chain or a ball chain. The tether may, in some examples, be attached loosely to the device via a ring that is smaller than the handles and thus trapped between them, or it may be smaller than a handle and the near end of a sheath for the clamp, also trapping it between them.

In some embodiments the entire device is disposable, while in others it is designed to be reused. In some embodiments, certain components are disposable while other components in the same embodiment may be reusable. In some embodiments, the components of the device may be comprised of one or more substances from the list including, but not limited to, silicone, plastic, metal, composites, or combinations thereof.

In some embodiments, the device is further comprised of an anchor that is comprised of a securing mechanism configured to be attached to a speculum or other surgical instrument or may be configured to adhere to skin or other surfaces and may be configured to hold the shaft or tether. The securing mechanism may be, but is not limited to, a mechanical clip, an adhesive patch, a pin, a needle to thread through a medium, a screw, an aperture through which the shaft of the device can be threaded (or said aperture can be opened to allow the shaft to be threaded) and/or a clasp. The securing mechanism may alternatively be a combination of the aforementioned components configured in a complementary way. For some examples of the device, the anchor includes a thread, hole, notch, clasp, or other means to secure the shaft or tether to the anchor, allowing the anchor to hold tension on the shaft or tether and by extension the article that the clasp is holding. In some embodiments, the anchor is configured to attach to a range of other surgical stabilizers or instruments including, but not limited to, a speculum. For some embodiments, the anchor is comprised in part of two overlapping cylinders wherein the two may be pushed together to expose and open an aperture into which the device or a portion thereof such as the shaft may be inserted.

In some embodiments the device may be configured to integrate with other tools for a variety of purposes, such as integrating with a gynecological speculum to reduce the tenaculum's profile and further improve the visibility through the speculum.

FIG. 1 is a perspective view of a cervical tenaculum device and anchor, in accordance with an embodiment of the invention.

In some embodiments, the device 100 comprises a shaft 102 (sometimes called the interior shaft) comprised of a first end 104 and a second end 106; a clamp 108 configured to be locked or unlocked attached to the first end 104 of the shaft; an actuator shaft 110 that is removably coupled to the shaft 102, slidable along the shaft 102, and configured to open and close the clamp 108. In some embodiments, the invention has two or more handles 112 that can be attached along the length of the actuator shaft 110 or shaft 102; in some of these embodiments the portion of the actuator shaft 110 that is between the handles 112 may be comprised of a removably attached coil 124 such that when the handles 112 are pulled towards each other the interior shaft 102 is pressed forward, which operates the clamp 108 such as by opening it or altering its configuration.

Some configurations of the device 100 involve a shaft 102, with a clamp 108 attached at one end, enveloped by the actuator shaft 110 further comprised of a coil 124, with two handles 112 positioned such that one is at the end of the shaft opposite the clamp 108 and the other is at a roughly medial (though it may vary if needed) position along the shaft. The handle 112 near the end of the shaft 102 is attached to the shaft 102, while the handle 112 in the medial position is attached to the actuator shaft 110 at the end of the coil 124, such that when a user presses on the handle 112 at the end of the shaft 102 while holding the handle 112 located at the medial position it pushes the clamp 108 through the actuator shaft 110 and compresses the coil 124 of the actuator shaft 110, which in turn pushes the clamp 108 out of the sheath 118. When the pressure is released, the coil 124 of the actuator shaft 110 extends and the sheath 118 closes the clamp 108.

In some embodiments the device 100 is further comprised of an actuator shaft 110 that may be operated by a twisting movement, push-pull movement, plunger, quick-release screw, or other means of engaging the actuator and in turn the clamp 108. In some embodiments the actuator shaft 110 may have multiple components allowing it to be held in various configurations such as being configured to remove the actuator shaft 110 or portions thereof once the clamp 108 is in place, remove the actuator shaft 110 and shaft 102 entirely once the clamp 108 is in place, or leave the entire device 100 in the patient. In some embodiments, the actuator shaft 110 may further comprise a compressible coil 124 that may be removably attached to the actuator shaft 110 or held on to it by a handle 112 or set screw 116.

In some embodiments, the device 100 is comprised of an internal shaft 102 with at least two ends 104, 106. At one end the clamp 108 may be attached. An external shaft, the actuator shaft 110, may envelop the internal shaft 102; in which case it may be a hollow cylindrical shape so that it wraps around the internal shaft 102. The interior or actuator shafts 102, 110 may be at least partially flexible and/or compressible; in some embodiments the actuator shaft 110 may be further comprised of a removably attached coil 124 of material such as, but not limited to, metal or a polymer that may partially envelop the actuator shaft 110. In some embodiments, there may be two handles 112 attached at either end of the actuator shaft 110 in order to attach it to the internal shaft 102; and in some of those embodiments the handles 112 may be attached by screwing onto the internal shaft 102 to keep the external actuator shaft 110 in place, or may be attached by a set-screw 116, clasp, or clamp; in some embodiments the actuator shaft 110 or a portion thereof may be trapped between them or held via pressure from set screws 116 against the interior shaft 102. In some embodiments the clamp 108 is expressed and opened by pressing on the rear handle 112 so that the actuator shaft 110 compresses and in turn pushes the internal shaft 102 forward.

In some embodiments the internal shaft 102 and actuator shaft 110 may be flexible such that they can be bent, allowing a practitioner to attach them to an anchor 114 or other grounding point while also moving them out of the way so that the practitioner can work. In some embodiments, the device 100 may have specific points along the internal shaft 102 and actuator shaft 110 where the bending occurs, while in other embodiments the full length of the shaft 102, 110 components may be flexible. The internal or actuator shafts 102, 110 may have threading in some embodiments that is configured to receive one or more handles 112; in other embodiments the handles 112 attach via set-screws 116 that place press the handle into the shaft. The shafts may be substantially cylindrical, flat, or other shapes. In at least one embodiment the shafts 102, 110 are substantially cylindrical and the interior shaft 102 is able to rotate within the actuator shaft 110, though in various embodiments there may be pressures preventing free rotation such as pressure applying the handle 112 to the shaft 102 via the set screw 116, or a close fit from the actuator shaft 110. In some embodiments the shafts 102, 110 are substantially straight, while in others one or both shafts 102, 110 may be curved or bent to enable specialized manipulation of tissue or articles.

In some embodiments, a practitioner or user engages the device by pressing on the actuator shaft 110 while pulling back on the shaft 102 or a handle 112 on the shaft 102, which in turn causes the clamp 108 to open. Some examples involve a sheath 118 attached to the actuator shaft 110 and overlapping the clamp 108 that fully covers it when the actuator shaft 110 is not being utilized, but when a user presses the handles 112 together it pushes the clamp 108 out of the sheath 118 which allows the clamp 108 to open; in such embodiments the clamp 108 may favor an opened position instead of closed or may even be a single piece of material which was constructed in an open position. Some embodiments may include a coil 124 between the handles 112 and at least partially enveloping the actuator shaft 110 to apply an opening pressure. The tips 120 of the clamp 108 can then be applied to a cervix or other article to be held, and once it is in a location the practitioner deems appropriate the actuator shaft 110 and handle(s) 112 can be released, which relieves the pressure keeping the clamp 108 open and closes the clamp 108, thereby taking hold of the article. The device 100 is then free to remain in the patient and grasping the article while the practitioner works utilizing other tools.

In some embodiments the clamp 108 is a jawed-clamp or other configuration wherein the clamp 108 may automatically favor a closed position over an open one and exerts tension on the points or pressure exerting areas of the clamp's tips 120. Some examples may have a complex clamp 108 structure wherein the clamp 108 has multiple modes that can be operated through the actuator shaft 110 and/or handles 112; such as locking the clamp 108 in its current position by twisting a handle 112 at a certain point, or it may have a click-in mechanism allowing it to hold pressure that can be quickly released. In some embodiments, the clamp 108 has a mechanism such as a screw, ratchet, or other variable tension means to place tension on the grasping means. In some embodiments the clamp 108 may be constructed as a single component wherein a piece of material, possibly a metal, is split and forked so that two tines are created, then bent towards each other, leaving a gap between them as necessary for the user, such that when the tines are pressed towards each other the tips 120 close the gap. In some embodiments, the tips 120 may contact each other, while in other embodiments they may overlap or pass each other. In some embodiments the mechanism is in the form of pointed tips 120 such as found in a common surgical tenaculum, or may be rounded, while in other embodiments it may involve a shaped pad or rod allowing it to displace the force over the surface it is grasping and diminish any trauma to the area or article being grasped. In some embodiments the clamp 108 may be a tether that encircles the area to be held like a noose or similar means. In some embodiments the clamp 108 is a pinch-based grasping means with two prongs, while in others it may have additional prongs as needed to sufficiently grasp and hold the article in question. In some embodiments, the clamp 108 is comprised of one or more hinges pivoted together such that when tension is placed on corresponding ends of the hinges the opposite ends are closed. In some embodiments, the clamp 108 is comprised of one or more hinges, such as scissor-hinges, that are connected with each other and operable against each other such that operating one hinge will operate another. In some embodiments the clamp 108 may be locked into position such that it does not exert any additional pressure once they are locked or closed to a certain degree; in other embodiments they may exert continuous closing or opening pressure. In some embodiments the clamp 108 may be at least partially flexible.

In some embodiments, the clamp 108 does not automatically favor a closed position but may favor a neutral or open position. Examples of such may feature a clamp 108 that is comprised of a single piece of material or it may have a spring integrated into the jaws of the clamp 108 that pushes it open. In some embodiments, the clamp 108 is also a scissors-style hinge mechanism wherein a distal end is designed to be a grasping end while a proximal end is the end engaged by the actuator shaft 110. In some embodiments, the clamp 108 may have a quick-release mechanism, retrieval cord, or other means of disengaging tension. In some embodiments, the scissors-style hinge clamp 108 may have a means of disengaging tension including a latch, catch, screw, and/or may be pushed on by the tether in order to release the tension.

In some embodiments the entire device 100 is disposable, while in others it is designed to be reused. In some embodiments certain components are disposable while other components in the same embodiment may be reusable. In some embodiments, the components of the device 100 may be comprised of one or more substances from the list including, but not limited to, silicone, plastic, metal, composites, or combinations thereof.

In some embodiments, the device 100 is further comprised of an anchor 114 that is comprised of a securing mechanism configured to be attached to a speculum or other surgical instrument or may be configured to adhere to skin or other surfaces and may be configured to hold the shafts 102, 110 or tether. The securing mechanism may be, but is not limited to, a mechanical clip, an adhesive patch, a pin, a needle to thread through a medium, a screw, an aperture 122 through which the shafts 102, 110 of the device 100 can be threaded (or said aperture 122 can be opened to allow the shaft to be threaded) and/or a clasp. The securing mechanism may alternatively be a combination of the aforementioned components configured in a complementary way. For some examples of the device 100, the anchor 114 includes a thread, hole, notch, clasp, or other means to secure the shaft or tether to the anchor 114, allowing the anchor 114 to hold tension on the shafts 102, 110 or tether and by extension the article that the clasp is holding. In some embodiments, the anchor 114 is configured to attach to a range of other surgical stabilizers or instruments including, but not limited to, a speculum. For some embodiments, the anchor 114 is comprised in part of two overlapping cylinders wherein the two may be pushed together to expose and open an aperture 122 into which the device 100 or a portion thereof such as the shafts 102, 110 may be inserted.

In some embodiments the device 100 may be configured to integrate with other tools for a variety of purposes, such as integrating with a gynecological speculum to reduce the tenaculum's profile and further improve the visibility through the speculum.

Figure 2:
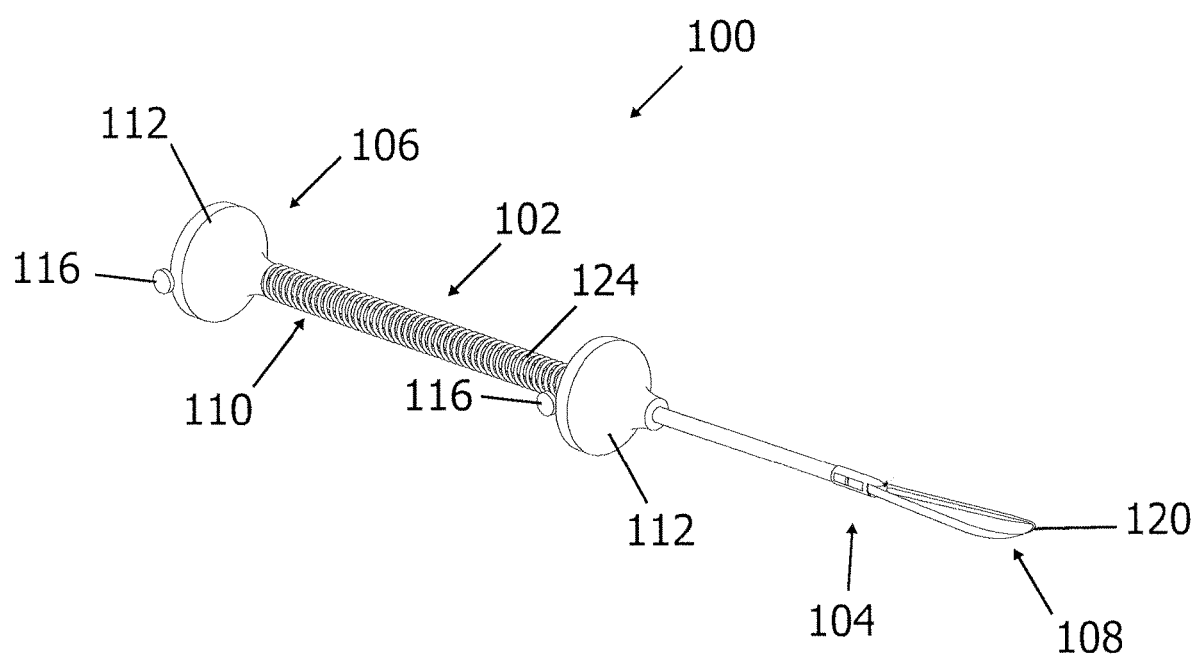
FIG. 2 is a perspective view of a cervical tenaculum device, in accordance with an embodiment of the invention.

FIG. 2 is a perspective view of a cervical tenaculum device and anchor, in accordance with an embodiment of the invention.

In some embodiments, the device 100 comprises a shaft 102 (sometimes called the interior shaft) comprised of a first end 104 and a second end 106; a clamp 108 configured to be locked or unlocked attached to the first end 104 of the shaft; an actuator shaft 110 that is removably coupled to the shaft 102, slidable along the shaft 102, and configured to open and close the clamp 108. In some embodiments, the invention has two or more handles 112 that can be attached along the length of the actuator shaft 110 or interior shaft 102; in some of these embodiments the portion of the actuator shaft 110 that is between the handles 112 may be comprised of a removably attached coil 124 such that when the handles 112 are pulled towards each other the interior shaft 102 is pressed forward, which operates the clamp 108 such as by opening it or altering its configuration.

Some configurations of the device 100 involve a shaft 102, with a clamp 108 attached at one end, enveloped by the actuator shaft 110 further comprised of a coil 124, with two handles 112 positioned such that one is at the end of the shaft opposite the clamp 108 and the other is at a roughly medial (though it may vary if needed) position along the shaft. The handle 112 near the end of the shaft 102 is attached to the shaft 102, while the handle 112 in the medial position is attached to the actuator shaft 110 at the end of the coil 124, such that when a user presses on the handle 112 at the end of the shaft 102 while holding the handle 112 located at the medial position it pushes the clamp 108 through the actuator shaft 110 and compresses the coil 124 of the actuator shaft 110, which in turn pushes the clamp 108 out of the sheath 118. When the pressure is released, the coil 124 of the actuator shaft 110 extends and the sheath 118 closes the clamp 108.

In some embodiments the device 100 is further comprised of an actuator shaft 110 that may be operated by a twisting movement, push-pull movement, plunger, quick-release screw, or other means of engaging the actuator and in turn the clamp 108. In some embodiments the actuator shaft 110 may have multiple components allowing it to be held in various configurations such as being configured to remove the actuator shaft 110 or portions thereof once the clamp 108 is in place, remove the actuator shaft 110 and shaft 102 entirely once the clamp 108 is in place, or leave the entire device 100 in the patient. In some embodiments, the actuator shaft 110 may further comprise a compressible coil 124 that may be removably attached to the actuator shaft 110 or held on to it by a handle 112 or set screw 116.

In some embodiments, the device 100 is comprised of an internal shaft 102 with at least two ends 104, 106. At one end the clamp 108 may be attached. An external shaft 110, the actuator shaft 110, may envelop the internal shaft 102; in which case it may be a hollow cylindrical shape so that it wraps around the internal shaft 102. The interior or actuator shafts 102, 110 may be at least partially flexible and/or compressible; in some embodiments the actuator shaft 110 may be further comprised of a removably attached coil 124 of material such as, but not limited to, metal or a polymer that may partially envelop the actuator shaft 110. In some embodiments, there may be two handles 112 attached at either end of the actuator shaft 110 in order to attach it to the internal shaft 102; and in some of those embodiments the handles 112 may be attached by screwing onto the internal shaft 102 to keep the external actuator shaft 110 in place, or may be attached by a set-screw 116, clasp, or clamp; in some embodiments the actuator shaft 110 or a portion thereof may be trapped between them or held via pressure from set screws 116 against the interior shaft 102. In some embodiments the clamp 108 is expressed and opened by pressing on the rear handle 112 so that the actuator shaft 110 compresses and in turn pushes the internal shaft 102 forward.

In some embodiments the internal 102 and actuator shafts 110 may be flexible such that they can be bent, allowing a practitioner to attach them to an anchor or other grounding point while also moving them out of the way so that the practitioner can work. In some embodiments, the device 100 may have specific points along the internal 102 and actuator shafts 110 where the bending occurs, while in other embodiments the full length of the shaft 102, 110 components may be flexible. The internal or actuator shafts 102, 110 may have threading in some embodiments that is configured to receive one or more handles 112; in other embodiments the handles 112 attach via set-screws 116 that place press the handle into the shaft. The shafts may be substantially cylindrical, flat, or other shapes. In at least one embodiment the shafts 102, 110 are substantially cylindrical and the interior shaft 102 is able to rotate within the actuator shaft 110, though in various embodiments there may be pressures preventing free rotation such as pressure applying the handle 112 to the shaft 102 via the set screw 116, or a close fit from the actuator shaft 110. In some embodiments the shafts 102, 110 are substantially straight, while in others one or both shafts 102 110 may be curved or bent to enable specialized manipulation of tissue or articles.

In some embodiments, a practitioner or user engages the device by pressing on the actuator shaft 110 while pulling back on the shaft 102 or a handle 112 on the shaft 102, which in turn causes the clamp 108 to open. Some examples involve a sheath 118 attached to the actuator shaft 110 and overlapping the clamp 108 that fully covers it when the actuator shaft 110 is not being utilized, but when a user presses the handles 112 together it pushes the clamp 108 out of the sheath 118 which allows the clamp 108 to open; in such embodiments the clamp 108 may favor an opened position instead of closed or may even be a single piece of material which was constructed in an open position. Some embodiments may include a coil 124 between the handles 112 and at least partially enveloping the actuator shaft 110 to apply an opening pressure. The tips 120 of the clamp 108 can then be applied to a cervix or other article to be held, and once it is in a location the practitioner deems appropriate the actuator shaft 110 and handle(s) 112 can be released, which relieves the pressure keeping the clamp 108 open and closes the clamp 108, thereby taking hold of the article. The device 100 is then free to remain in the patient and grasping the article while the practitioner works utilizing other tools.

In some embodiments the clamp 108 is a jawed-clamp or other configuration wherein the clamp 108 may automatically favor a closed position over an open one and exerts tension on the points or pressure exerting areas of the clamp's tips 120. Some examples may have a complex clamp 108 structure wherein the clamp 108 has multiple modes that can be operated through the actuator shaft 110 and/or handles 112; such as locking the clamp 108 in its current position by twisting a handle 112 at a certain point, or it may have a click-in mechanism allowing it to hold pressure that can be quickly released. In some embodiments, the clamp 108 has a mechanism such as a screw, ratchet, or other variable tension means to place tension on the grasping means. In some embodiments the clamp 108 may be constructed as a single component wherein a piece of material, possibly a metal, is split and forked so that two tines are created, then bent towards each other, leaving a gap between them as necessary for the user, such that when the tines are pressed towards each other the tips 120 close the gap. In some embodiments, the tips 120 may contact each other, while in other embodiments they may overlap or pass each other. In some embodiments the mechanism is in the form of pointed tips 120 such as found in a common surgical tenaculum, or may be rounded, while in other embodiments it may involve a shaped pad or rod allowing it to displace the force over the surface it is grasping and diminish any trauma to the area or article being grasped. In some embodiments the clamp 108 may be a tether that encircles the area to be held like a noose or similar means. In some embodiments the clamp 108 is a pinch-based grasping means with two prongs, while in others it may have additional prongs as needed to sufficiently grasp and hold the article in question. In some embodiments, the clamp 108 is comprised of one or more hinges pivoted together such that when tension is placed on corresponding ends of the hinges the opposite ends are closed. In some embodiments, the clamp 108 is comprised of one or more hinges, such as scissor-hinges, that are connected with each other and operable against each other such that operating one hinge will operate another. In some embodiments the clamp 108 may be locked into position such that it does not exert any additional pressure once they are locked or closed to a certain degree; in other embodiments they may exert continuous closing or opening pressure. In some embodiment the clamp 108 may be at least partially flexible.

In some embodiments, the clamp 108 does not automatically favor a closed position but may favor a neutral or open position. Examples of such may feature a clamp 108 that is comprised of a single piece of material or it may have a spring integrated into the jaws of the clamp 108 that pushes it open. In some embodiments, the clamp 108 is also a scissors-style hinge mechanism wherein a distal end is designed to be a grasping end while a proximal end is the end engaged by the actuator shaft 110. In some embodiments, the clamp 108 may have a quick-release mechanism, retrieval cord, or other means of disengaging tension. In some embodiments, the scissors-style hinge clamp 108 may have a means of disengaging tension including a latch, catch, screw, and/or may be pushed on by the tether in order to release the tension.

In some embodiments the entire device 100 is disposable, while in others it is designed to be reused. In some embodiments certain components are disposable while other components in the same embodiment may be reusable. In some embodiments, the components of the device 100 may be comprised of one or more substances from the list including, but not limited to, silicone, plastic, metal, composites, or combinations thereof.

In some embodiments, the device 100 is further comprised of an anchor that is comprised of a securing mechanism configured to be attached to a speculum or other surgical instrument or may be configured to adhere to skin or other surfaces and may be configured to hold the shafts 102, 110 or tether. The securing mechanism may be, but is not limited to, a mechanical clip, an adhesive patch, a pin, a needle to thread through a medium, a screw, an aperture through which the shafts 102, 110 of the device 100 can be threaded (or said aperture can be opened to allow the shaft to be threaded) and/or a clasp. The securing mechanism may alternatively be a combination of the aforementioned components configured in a complementary way. For some examples of the device 100, the anchor includes a thread, hole, notch, clasp, or other means to secure the shaft or tether to the anchor, allowing the anchor to hold tension on the shaft or tether and by extension the article that the clasp is holding. In some embodiments, the anchor is configured to attach to a range of other surgical stabilizers or instruments including, but not limited to, a speculum. For some embodiments, the anchor is comprised in part of two overlapping cylinders wherein the two may be pushed together to expose and open an aperture into which the device 100 or a portion thereof such as the shafts 102, 110 may be inserted.

In some embodiments the device 100 may be configured to integrate with other tools for a variety of purposes, such as integrating with a gynecological speculum to reduce the tenaculum's profile and further improve the visibility through the speculum.

Figure 3:
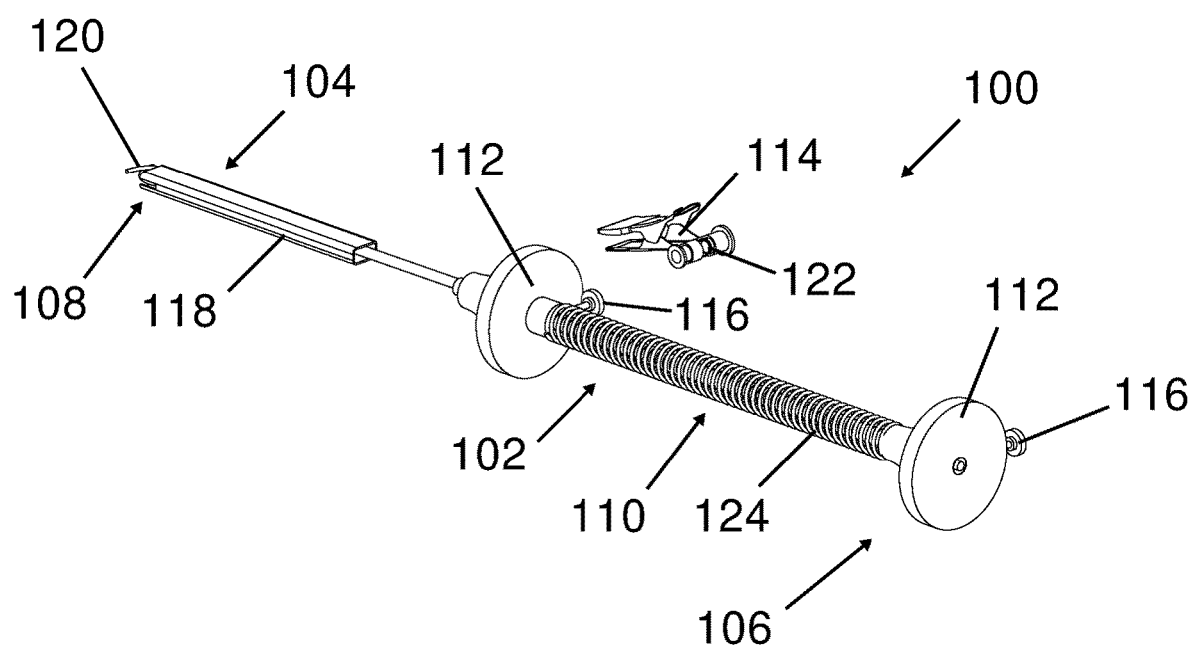
FIG. 3 is a perspective view of a cervical tenaculum device and anchor, in accordance with an embodiment of the invention.

FIG. 3 is a perspective view of a cervical tenaculum device and anchor, in accordance with an embodiment of the invention.

In some embodiments, the device 100 comprises a shaft 102 (sometimes called the interior shaft) comprised of a first end 104 and a second end 106; a clamp 108 configured to be locked or unlocked attached to the first end 104 of the shaft; an actuator shaft 110 that is removably coupled to the shaft 102, slidable along the shaft 102, and configured to open and close the clamp 108. In some embodiments, the invention has two or more handles 112 that can be attached along the length of the actuator shaft 110 or shaft 102; in some of these embodiments the portion of the actuator shaft 110 that is between the handles 112 may be comprised of a removably attached coil 124 such that when the handles 112 are pulled towards each other the interior shaft 102 is pressed forward, which operates the clamp 108 such as by opening it or altering its configuration.

Some configurations of the device 100 involve a shaft 102, with a clamp 108 attached at one end, enveloped by the actuator shaft 110 further comprised of a coil 124, with two handles 112 positioned such that one is at the end of the shaft opposite the clamp 108 and the other is at a roughly medial (though it may vary if needed) position along the shaft. The handle 112 near the end of the shaft 102 is attached to the shaft 102, while the handle 112 in the medial position is attached to the actuator shaft 110 at the end of the coil 124, such that when a user presses on the handle 112 at the end of the shaft 102 while holding the handle 112 located at the medial position it pushes the clamp 108 through the actuator shaft 110 and compresses the coil 124 of the actuator shaft 110, which in turn pushes the clamp 108 out of the sheath 118. When the pressure is released, the coil 124 of the actuator shaft 110 extends and the sheath 118 closes the clamp 108.

In some embodiments the device 100 is further comprised of an actuator shaft 110 that may be operated by a twisting movement, push-pull movement, plunger, quick-release screw, or other means of engaging the actuator and in turn the clamp 108. In some embodiments the actuator shaft 110 may have multiple components allowing it to be held in various configurations such as being configured to remove the actuator shaft 110 or portions thereof once the clamp 108 is in place, remove the actuator shaft 110 and shaft 102 entirely once the clamp 108 is in place, or leave the entire device 100 in the patient. In some embodiments, the actuator shaft 110 may further comprise a compressible coil 124 that may be removably attached to the actuator shaft 110 or held on to it by a handle 112 or set screw 116.

In some embodiments, the device 100 is comprised of an internal shaft 102 with at least two ends 104, 106. At one end the clamp 108 may be attached. An external shaft 110, the actuator shaft 110, may envelop the internal shaft 102; in which case it may be a hollow cylindrical shape so that it wraps around the internal shaft 102. The interior or actuator shafts 102, 110 may be at least partially flexible and/or compressible; in some embodiments the actuator shaft 110 may be further comprised of a removably attached coil 124 of material such as, but not limited to, metal or a polymer that may partially envelop the actuator shaft 110. In some embodiments, there may be two handles 112 attached at either end of the actuator shaft 110 in order to attach it to the internal shaft 102; and in some of those embodiments the handles 112 may be attached by screwing onto the internal shaft 102 to keep the external actuator shaft 110 in place, or may be attached by a set-screw 116, clasp, or clamp; in some embodiments the actuator shaft 110 or a portion thereof may be trapped between them or held via pressure from set screws 116 against the interior shaft 102. In some embodiments the clamp 108 is expressed and opened by pressing on the rear handle 112 so that the actuator shaft 110 compresses and in turn pushes the internal shaft 102 forward.

In some embodiments the internal 102 and actuator shafts 110 may be flexible such that they can be bent, allowing a practitioner to attach them to an anchor 114 or other grounding point while also moving them out of the way so that the practitioner can work. In some embodiments, the device 100 may have specific points along the internal 102 and actuator shafts 110 where the bending occurs, while in other embodiments the full length of the shaft 102, 110 components may be flexible. The internal or actuator shafts 102, 110 may have threading in some embodiments that is configured to receive one or more handles 112; in other embodiments the handles 112 attach via set-screws 116 that place press the handle into the shaft. The shafts may be substantially cylindrical, flat, or other shapes. In at least one embodiment the shafts 102, 110 are substantially cylindrical and the interior shaft 102 is able to rotate within the actuator shaft 110, though in various embodiments there may be pressures preventing free rotation such as pressure applying the handle 112 to the shaft 102 via the set screw 116, or a close fit from the actuator shaft 110. In some embodiments the shafts 102, 110 are substantially straight, while in others one or both shafts 102 110 may be curved or bent to enable specialized manipulation of tissue or articles.

In some embodiments, a practitioner or user engages the device by pressing on the actuator shaft 110 while pulling back on the shaft 102 or a handle 112 on the shaft 102, which in turn causes the clamp 108 to open. Some examples involve a sheath 118 attached to the actuator shaft 110 and overlapping the clamp 108 that fully covers it when the actuator shaft 110 is not being utilized, but when a user presses the handles 112 together it pushes the clamp 108 out of the sheath 118 which allows the clamp 108 to open; in such embodiments the clamp 108 may favor an opened position instead of closed or may even be a single piece of material which was constructed in an open position. Some embodiments may include a coil 124 between the handles 112 and at least partially enveloping the actuator shaft 110 to apply an opening pressure. The tips 120 of the clamp 108 can then be applied to a cervix or other article to be held, and once it is in a location the practitioner deems appropriate the actuator shaft 110 and handle(s) 112 can be released, which relieves the pressure keeping the clamp 108 open and closes the clamp 108, thereby taking hold of the article. The device 100 is then free to remain in the patient and grasping the article while the practitioner works utilizing other tools.

In some embodiments the clamp 108 is a jawed-clamp or other configuration wherein the clamp 108 may automatically favor a closed position over an open one and exerts tension on the points or pressure exerting areas of the clamp's tips 120. Some examples may have a complex clamp 108 structure wherein the clamp 108 has multiple modes that can be operated through the actuator shaft 110 and/or handles 112; such as locking the clamp 108 in its current position by twisting a handle 112 at a certain point, or it may have a click-in mechanism allowing it to hold pressure that can be quickly released. In some embodiments, the clamp 108 has a mechanism such as a screw, ratchet, or other variable tension means to place tension on the grasping means. In some embodiments the clamp 108 may be constructed as a single component wherein a piece of material, possibly a metal, is split and forked so that two tines are created, then bent towards each other, leaving a gap between them as necessary for the user, such that when the tines are pressed towards each other the tips 120 close the gap. In some embodiments, the tips 120 may contact each other, while in other embodiments they may overlap or pass each other. In some embodiments the mechanism is in the form of pointed tips 120 such as found in a common surgical tenaculum, or may be rounded, while in other embodiments it may involve a shaped pad or rod allowing it to displace the force over the surface it is grasping and diminish any trauma to the area or article being grasped. In some embodiments the clamp 108 may be a tether that encircles the area to be held like a noose or similar means. In some embodiments the clamp 108 is a pinch-based grasping means with two prongs, while in others it may have additional prongs as needed to sufficiently grasp and hold the article in question. In some embodiments, the clamp 108 is comprised of one or more hinges pivoted together such that when tension is placed on corresponding ends of the hinges the opposite ends are closed. In some embodiments, the clamp 108 is comprised of one or more hinges, such as scissor-hinges, that are connected with each other and operable against each other such that operating one hinge will operate another. In some embodiments the clamp 108 may be locked into position such that it does not exert any additional pressure once they are locked or closed to a certain degree; in other embodiments they may exert continuous closing or opening pressure. In some embodiment the clamp 108 may be at least partially flexible.

In some embodiments, the clamp 108 does not automatically favor a closed position but may favor a neutral or open position. Examples of such may feature a clamp 108 that is comprised of a single piece of material or it may have a spring integrated into the jaws of the clamp 108 that pushes it open. In some embodiments, the clamp 108 is also a scissors-style hinge mechanism wherein a distal end is designed to be a grasping end while a proximal end is the end engaged by the actuator shaft 110. In some embodiments, the clamp 108 may have a quick-release mechanism, retrieval cord, or other means of disengaging tension. In some embodiments, the scissors-style hinge clamp 108 may have a means of disengaging tension including a latch, catch, screw, and/or may be pushed on by the tether in order to release the tension.

In some embodiments the entire device 100 is disposable, while in others it is designed to be reused. In some embodiments certain components are disposable while other components in the same embodiment may be reusable. In some embodiments, the components of the device 100 may be comprised of one or more substances from the list including, but not limited to, silicone, plastic, metal, composites, or combinations thereof.

In some embodiments, the device 100 is further comprised of an anchor 114 that is comprised of a securing mechanism configured to be attached to a speculum or other surgical instrument or may be configured to adhere to skin or other surfaces and may be configured to hold the shafts 102, 110 or tether. The securing mechanism may be, but is not limited to, a mechanical clip, an adhesive patch, a pin, a needle to thread through a medium, a screw, an aperture 122 through which the shafts 102, 110 of the device 100 can be threaded (or said aperture 122 can be opened to allow the shaft to be threaded) and/or a clasp. The securing mechanism may alternatively be a combination of the aforementioned components configured in a complementary way. For some examples of the device 100, the anchor 114 includes a thread, hole, notch, clasp, or other means to secure the shaft or tether to the anchor 114, allowing the anchor 114 to hold tension on the shaft 102, 110 or tether and by extension the article that the clasp is holding. In some embodiments, the anchor 114 is configured to attach to a range of other surgical stabilizers or instruments including, but not limited to, a speculum. For some embodiments, the anchor 114 is comprised in part of two overlapping cylinders wherein the two may be pushed together to expose and open an aperture 122 into which the device 100 or a portion thereof such as the shafts 102, 110 may be inserted.

In some embodiments the device 100 may be configured to integrate with other tools for a variety of purposes, such as integrating with a gynecological speculum to reduce the tenaculum's profile and further improve the visibility through the speculum.

Figure 4:
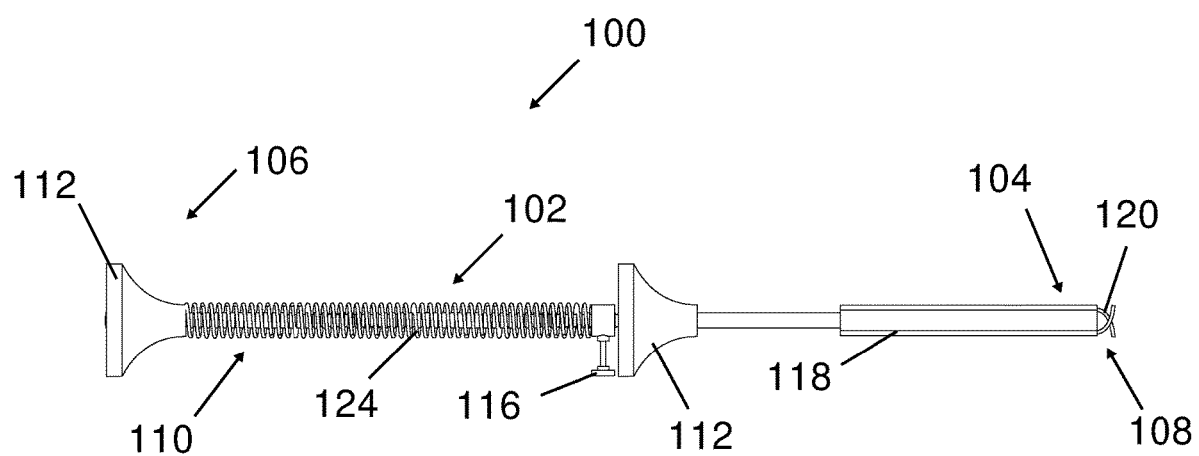
FIG. 4 is a side view of a cervical tenaculum device, in accordance with an embodiment of the invention.

FIG. 4 is a side view of a cervical tenaculum device, in accordance with an embodiment of the invention.

In some embodiments, the device 100 comprises a shaft 102 (sometimes called the interior shaft) comprised of a first end 104 and a second end 106; a clamp 108 configured to be locked or unlocked attached to the first end 104 of the shaft; an actuator shaft 110 that is removably coupled to the shaft 102, slidable along the shaft 102, and configured to open and close the clamp 108. In some embodiments, the invention has two or more handles 112 that can be attached along the length of the actuator shaft 110 or shaft 102; in some of these embodiments the portion of the actuator shaft 110 that is between the handles 112 may be comprised of a removably attached coil 124 such that when the handles 112 are pulled towards each other the interior shaft 102 is pressed forward, which operates the clamp 108 such as by opening it or altering its configuration.

Some configurations of the device 100 involve a shaft 102, with a clamp 108 attached at one end, enveloped by the actuator shaft 110 further comprised of a coil 124, with two handles 112 positioned such that one is at the end of the shaft opposite the clamp 108 and the other is at a roughly medial (though it may vary if needed) position along the shaft. The handle 112 near the end of the shaft 102 is attached to the shaft 102, while the handle 112 in the medial position is attached to the actuator shaft 110 at the end of the coil 124, such that when a user presses on the handle 112 at the end of the shaft 102 while holding the handle 112 located at the medial position it pushes the clamp 108 through the actuator shaft 110 and compresses the coil 124 of the actuator shaft 110, which in turn pushes the clamp 108 out of the sheath 118. When the pressure is released, the coil 124 of the actuator shaft 110 extends and the sheath 118 closes the clamp 108.

In some embodiments the device 100 is further comprised of an actuator shaft 110 that may be operated by a twisting movement, push-pull movement, plunger, quick-release screw, or other means of engaging the actuator and in turn the clamp 108. In some embodiments the actuator shaft 110 may have multiple components allowing it to be held in various configurations such as being configured to remove the actuator shaft 110 or portions thereof once the clamp 108 is in place, remove the actuator shaft 110 and shaft 102 entirely once the clamp 108 is in place, or leave the entire device 100 in the patient. In some embodiments, the actuator shaft 110 may further comprise a compressible coil 124 that may be removably attached to the actuator shaft 110 or held on to it by a handle 112 or set screw 116.

In some embodiments, the device 100 is comprised of an internal shaft 102 with at least two ends 104, 106. At one end the clamp 108 may be attached. An external shaft 110, the actuator shaft 110, may envelop the internal shaft 102; in which case it may be a hollow cylindrical shape so that it wraps around the internal shaft 102. The interior or actuator shafts 102, 110 may be at least partially flexible and/or compressible; in some embodiments the actuator shaft 110 may be further comprised of a removably attached coil 124 of material such as, but not limited to, metal or a polymer that may partially envelop the actuator shaft 110. In some embodiments, there may be two handles 112 attached at either end of the actuator shaft 110 in order to attach it to the internal shaft 102; and in some of those embodiments the handles 112 may be attached by screwing onto the internal shaft 102 to keep the external actuator shaft 110 in place, or may be attached by a set-screw 116, clasp, or clamp; in some embodiments the actuator shaft 110 or a portion thereof may be trapped between them or held via pressure from set screws 116 against the interior shaft 102. In some embodiments the clamp 108 is expressed and opened by pressing on the rear handle 112 so that the actuator shaft 110 compresses and in turn pushes the internal shaft 102 forward.

In some embodiments the internal 102 and actuator shafts 110 may be flexible such that they can be bent, allowing a practitioner to attach them to an anchor or other grounding point while also moving them out of the way so that the practitioner can work. In some embodiments, the device 100 may have specific points along the internal 102 and actuator shafts 110 where the bending occurs, while in other embodiments the full length of the shaft 102, 110 components may be flexible. The internal or actuator shafts 102, 110 may have threading in some embodiments that is configured to receive one or more handles 112; in other embodiments the handles 112 attach via set-screws 116 that place press the handle into the shaft. The shafts may be substantially cylindrical, flat, or other shapes. In at least one embodiment the shafts 102, 110 are substantially cylindrical and the interior shaft 102 is able to rotate within the actuator shaft 110, though in various embodiments there may be pressures preventing free rotation such as pressure applying the handle 112 to the shaft 102 via the set screw 116, or a close fit from the actuator shaft 110. In some embodiments the shafts 102, 110 are substantially straight, while in others one or both shafts 102 110 may be curved or bent to enable specialized manipulation of tissue or articles.

In some embodiments, a practitioner or user engages the device by pressing on the actuator shaft 110 while pulling back on the shaft 102 or a handle 112 on the shaft 102, which in turn causes the clamp 108 to open. Some examples involve a sheath 118 attached to the actuator shaft 110 and overlapping the clamp 108 that fully covers it when the actuator shaft 110 is not being utilized, but when a user presses the handles 112 together it pushes the clamp 108 out of the sheath 118 which allows the clamp 108 to open; in such embodiments the clamp 108 may favor an opened position instead of closed or may even be a single piece of material which was constructed in an open position. Some embodiments may include a coil 124 between the handles 112 and at least partially enveloping the actuator shaft 110 to apply an opening pressure. The tips 120 of the clamp 108 can then be applied to a cervix or other article to be held, and once it is in a location the practitioner deems appropriate the actuator shaft 110 and handle(s) 112 can be released, which relieves the pressure keeping the clamp 108 open and closes the clamp 108, thereby taking hold of the article. The device 100 is then free to remain in the patient and grasping the article while the practitioner works utilizing other tools.

In some embodiments the clamp 108 is a jawed-clamp or other configuration wherein the clamp 108 may automatically favor a closed position over an open one and exerts tension on the points or pressure exerting areas of the clamp's tips 120. Some examples may have a complex clamp 108 structure wherein the clamp 108 has multiple modes that can be operated through the actuator shaft 110 and/or handles 112; such as locking the clamp 108 in its current position by twisting a handle 112 at a certain point, or it may have a click-in mechanism allowing it to hold pressure that can be quickly released. In some embodiments, the clamp 108 has a mechanism such as a screw, ratchet, or other variable tension means to place tension on the grasping means. In some embodiments the clamp 108 may be constructed as a single component wherein a piece of material, possibly a metal, is split and forked so that two tines are created, then bent towards each other, leaving a gap between them as necessary for the user, such that when the tines are pressed towards each other the tips 120 close the gap. In some embodiments, the tips 120 may contact each other, while in other embodiments they may overlap or pass each other. In some embodiments the mechanism is in the form of pointed tips 120 such as found in a common surgical tenaculum, or may be rounded, while in other embodiments it may involve a shaped pad or rod allowing it to displace the force over the surface it is grasping and diminish any trauma to the area or article being grasped. In some embodiments the clamp 108 may be a tether that encircles the area to be held like a noose or similar means. In some embodiments the clamp 108 is a pinch-based grasping means with two prongs, while in others it may have additional prongs as needed to sufficiently grasp and hold the article in question. In some embodiments, the clamp 108 is comprised of one or more hinges pivoted together such that when tension is placed on corresponding ends of the hinges the opposite ends are closed. In some embodiments, the clamp 108 is comprised of one or more hinges, such as scissor-hinges, that are connected with each other and operable against each other such that operating one hinge will operate another. In some embodiments the clamp 108 may be locked into position such that it does not exert any additional pressure once they are locked or closed to a certain degree; in other embodiments they may exert continuous closing or opening pressure. In some embodiment the clamp 108 may be at least partially flexible.

In some embodiments, the clamp 108 does not automatically favor a closed position but may favor a neutral or open position. Examples of such may feature a clamp 108 that is comprised of a single piece of material or it may have a spring integrated into the jaws of the clamp 108 that pushes it open. In some embodiments, the clamp 108 is also a scissors-style hinge mechanism wherein a distal end is designed to be a grasping end while a proximal end is the end engaged by the actuator shaft 110. In some embodiments, the clamp 108 may have a quick-release mechanism, retrieval cord, or other means of disengaging tension. In some embodiments, the scissors-style hinge clamp 108 may have a means of disengaging tension including a latch, catch, screw, and/or may be pushed on by the tether in order to release the tension.

In some embodiments the entire device 100 is disposable, while in others it is designed to be reused. In some embodiments certain components are disposable while other components in the same embodiment may be reusable. In some embodiments, the components of the device 100 may be comprised of one or more substances from the list including, but not limited to, silicone, plastic, metal, composites, or combinations thereof.

In some embodiments, the device 100 is further comprised of an anchor that is comprised of a securing mechanism configured to be attached to a speculum or other surgical instrument or may be configured to adhere to skin or other surfaces and may be configured to hold the shafts 102, 110 or tether. The securing mechanism may be, but is not limited to, a mechanical clip, an adhesive patch, a pin, a needle to thread through a medium, a screw, an aperture through which the shafts 102, 110 of the device 100 can be threaded (or said aperture can be opened to allow the shaft to be threaded) and/or a clasp. The securing mechanism may alternatively be a combination of the aforementioned components configured in a complementary way. For some examples of the device 100, the anchor includes a thread, hole, notch, clasp, or other means to secure the shaft or tether to the anchor, allowing the anchor to hold tension on the shaft or tether and by extension the article that the clasp is holding. In some embodiments, the anchor is configured to attach to a range of other surgical stabilizers or instruments including, but not limited to, a speculum. For some embodiments, the anchor is comprised in part of two overlapping cylinders wherein the two may be pushed together to expose and open an aperture into which the device 100 or a portion thereof such as the shafts 102, 110 may be inserted.

In some embodiments the device 100 may be configured to integrate with other tools for a variety of purposes, such as integrating with a gynecological speculum to reduce the tenaculum's profile and further improve the visibility through the speculum.

Figure 5:
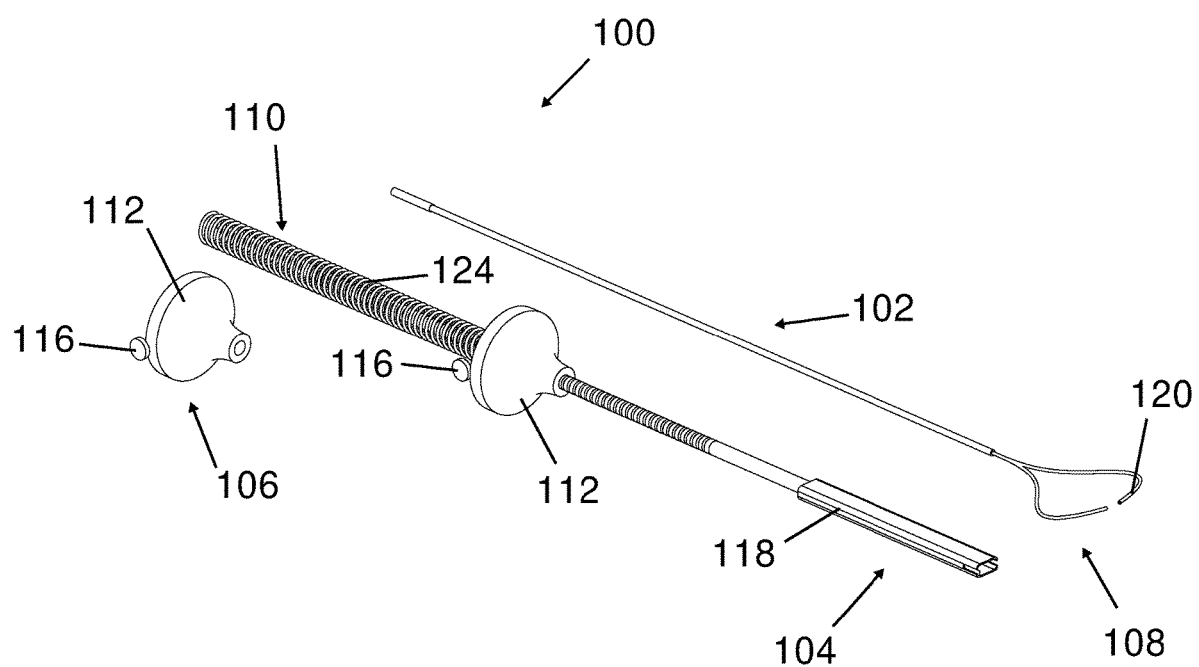
FIG. 5 is a perspective view of a disassembled cervical tenaculum device, in accordance with an embodiment of the invention.

FIG. 5 is a perspective view of a disassembled cervical tenaculum device, in accordance with an embodiment of the invention.

In some embodiments, the device 100 comprises a shaft 102 (sometimes called the interior shaft) comprised of a first end 104 and a second end 106; a clamp 108 configured to be locked or unlocked attached to the first end 104 of the shaft; an actuator shaft 110 that is removably coupled to the shaft 102, slidable along the shaft 102, and configured to open and close the clamp 108. In some embodiments, the invention has two or more handles 112 that can be attached along the length of the actuator shaft 110 or shaft 102; in some of these embodiments the portion of the actuator shaft 110 that is between the handles 112 may be comprised of a removably attached coil 124 such that when the handles 112 are pulled towards each other the interior shaft 102 is pressed forward, which operates the clamp 108 such as by opening it or altering its configuration.

Some configurations of the device 100 involve a shaft 102, with a clamp 108 attached at one end, enveloped by the actuator shaft 110 further comprised of a coil 124, with two handles 112 positioned such that one is at the end of the shaft opposite the clamp 108 and the other is at a roughly medial (though it may vary if needed) position along the shaft. The handle 112 near the end of the shaft 102 is attached to the shaft 102, while the handle 112 in the medial position is attached to the actuator shaft 110 at the end of the coil 124, such that when a user presses on the handle 112 at the end of the shaft 102 while holding the handle 112 located at the medial position it pushes the clamp 108 through the actuator shaft 110 and compresses the coil 124 of the actuator shaft 110, which in turn pushes the clamp 108 out of the sheath 118. When the pressure is released, the coil 124 of the actuator shaft 110 extends and the sheath 118 closes the clamp 108.

In some embodiments the device 100 is further comprised of an actuator shaft 110 that may be operated by a twisting movement, push-pull movement, plunger, quick-release screw, or other means of engaging the actuator and in turn the clamp 108. In some embodiments the actuator shaft 110 may have multiple components allowing it to be held in various configurations such as being configured to remove the actuator shaft 110 or portions thereof once the clamp 108 is in place, remove the actuator shaft 110 and shaft 102 entirely once the clamp 108 is in place, or leave the entire device 100 in the patient. In some embodiments, the actuator shaft 110 may further comprise a compressible coil 124 that may be removably attached to the actuator shaft 110 or held on to it by a handle 112 or set screw 116.

In some embodiments, the device 100 is comprised of an internal shaft 102 with at least two ends 104, 106. At one end the clamp 108 may be attached. An external shaft 110, the actuator shaft 110, may envelop the internal shaft 102; in which case it may be a hollow cylindrical shape so that it wraps around the internal shaft 102. The interior or actuator shafts 102, 110 may be at least partially flexible and/or compressible; in some embodiments the actuator shaft 110 may be further comprised of a removably attached coil 124 of material such as, but not limited to, metal or a polymer that may partially envelop the actuator shaft 110. In some embodiments, there may be two handles 112 attached at either end of the actuator shaft 110 in order to attach it to the internal shaft 102; and in some of those embodiments the handles 112 may be attached by screwing onto the internal shaft 102 to keep the external actuator shaft 110 in place, or may be attached by a set-screw 116, clasp, or clamp; in some embodiments the actuator shaft 110 or a portion thereof may be trapped between them or held via pressure from set screws 116 against the interior shaft 102. In some embodiments the clamp 108 is expressed and opened by pressing on the rear handle 112 so that the actuator shaft 110 compresses and in turn pushes the internal shaft 102 forward.

In some embodiments the internal 102 and actuator shafts 110 may be flexible such that they can be bent, allowing a practitioner to attach them to an anchor or other grounding point while also moving them out of the way so that the practitioner can work. In some embodiments, the device 100 may have specific points along the internal 102 and actuator shafts 110 where the bending occurs, while in other embodiments the full length of the shaft 102, 110 components may be flexible. The internal or actuator shafts 102, 110 may have threading in some embodiments that is configured to receive one or more handles 112; in other embodiments the handles 112 attach via set-screws 116 that place press the handle into the shaft. The shafts may be substantially cylindrical, flat, or other shapes. In at least one embodiment the shafts 102, 110 are substantially cylindrical and the interior shaft 102 is able to rotate within the actuator shaft 110, though in various embodiments there may be pressures preventing free rotation such as pressure applying the handle 112 to the shaft 102 via the set screw 116, or a close fit from the actuator shaft 110. In some embodiments the shafts 102, 110 are substantially straight, while in others one or both shafts 102 110 may be curved or bent to enable specialized manipulation of tissue or articles.

In some embodiments, a practitioner or user engages the device by pressing on the actuator shaft 110 while pulling back on the shaft 102 or a handle 112 on the shaft 102, which in turn causes the clamp 108 to open. Some examples involve a sheath 118 attached to the actuator shaft 110 and overlapping the clamp 108 that fully covers it when the actuator shaft 110 is not being utilized, but when a user presses the handles 112 together it pushes the clamp 108 out of the sheath 118 which allows the clamp 108 to open; in such embodiments the clamp 108 may favor an opened position instead of closed or may even be a single piece of material which was constructed in an open position. Some embodiments may include a coil 124 between the handles 112 and at least partially enveloping the actuator shaft 110 to apply an opening pressure. The tips 120 of the clamp 108 can then be applied to a cervix or other article to be held, and once it is in a location the practitioner deems appropriate the actuator shaft 110 and handle(s) 112 can be released, which relieves the pressure keeping the clamp 108 open and closes the clamp 108, thereby taking hold of the article. The device 100 is then free to remain in the patient and grasping the article while the practitioner works utilizing other tools.

In some embodiments the clamp 108 is a jawed-clamp or other configuration wherein the clamp 108 may automatically favor a closed position over an open one and exerts tension on the points or pressure exerting areas of the clamp's tips 120. Some examples may have a complex clamp 108 structure wherein the clamp 108 has multiple modes that can be operated through the actuator shaft 110 and/or handles 112; such as locking the clamp 108 in its current position by twisting a handle 112 at a certain point, or it may have a click-in mechanism allowing it to hold pressure that can be quickly released. In some embodiments, the clamp 108 has a mechanism such as a screw, ratchet, or other variable tension means to place tension on the grasping means. In some embodiments the clamp 108 may be constructed as a single component wherein a piece of material, possibly a metal, is split and forked so that two tines are created, then bent towards each other, leaving a gap between them as necessary for the user, such that when the tines are pressed towards each other the tips 120 close the gap. In some embodiments, the tips 120 may contact each other, while in other embodiments they may overlap or pass each other. In some embodiments the mechanism is in the form of pointed tips 120 such as found in a common surgical tenaculum, or may be rounded, while in other embodiments it may involve a shaped pad or rod allowing it to displace the force over the surface it is grasping and diminish any trauma to the area or article being grasped. In some embodiments the clamp 108 may be a tether that encircles the area to be held like a noose or similar means. In some embodiments the clamp 108 is a pinch-based grasping means with two prongs, while in others it may have additional prongs as needed to sufficiently grasp and hold the article in question. In some embodiments, the clamp 108 is comprised of one or more hinges pivoted together such that when tension is placed on corresponding ends of the hinges the opposite ends are closed. In some embodiments, the clamp 108 is comprised of one or more hinges, such as scissor-hinges, that are connected with each other and operable against each other such that operating one hinge will operate another. In some embodiments the clamp 108 may be locked into position such that it does not exert any additional pressure once they are locked or closed to a certain degree; in other embodiments they may exert continuous closing or opening pressure. In some embodiment the clamp may be at least partially flexible.

In some embodiments, the clamp 108 does not automatically favor a closed position but may favor a neutral or open position. Examples of such may feature a clamp 108 that is comprised of a single piece of material or it may have a spring integrated into the jaws of the clamp 108 that pushes it open. In some embodiments, the clamp 108 is also a scissors-style hinge mechanism wherein a distal end is designed to be a grasping end while a proximal end is the end engaged by the actuator shaft 110. In some embodiments, the clamp 108 may have a quick-release mechanism, retrieval cord, or other means of disengaging tension. In some embodiments, the scissors-style hinge clamp 108 may have a means of disengaging tension including a latch, catch, screw, and/or may be pushed on by the tether in order to release the tension.

In some embodiments the entire device 100 is disposable, while in others it is designed to be reused. In some embodiments certain components are disposable while other components in the same embodiment may be reusable. In some embodiments, the components of the device 100 may be comprised of one or more substances from the list including, but not limited to, silicone, plastic, metal, composites, or combinations thereof.

In some embodiments, the device 100 is further comprised of an anchor that is comprised of a securing mechanism configured to be attached to a speculum or other surgical instrument or may be configured to adhere to skin or other surfaces and may be configured to hold the shafts 102, 110 or tether. The securing mechanism may be, but is not limited to, a mechanical clip, an adhesive patch, a pin, a needle to thread through a medium, a screw, an aperture through which the shafts 102, 110 of the device 100 can be threaded (or said aperture can be opened to allow the shaft to be threaded) and/or a clasp. The securing mechanism may alternatively be a combination of the aforementioned components configured in a complementary way. For some examples of the device 100, the anchor includes a thread, hole, notch, clasp, or other means to secure the shaft or tether to the anchor, allowing the anchor to hold tension on the shaft or tether and by extension the article that the clasp is holding. In some embodiments, the anchor is configured to attach to a range of other surgical stabilizers or instruments including, but not limited to, a speculum. For some embodiments, the anchor is comprised in part of two overlapping cylinders wherein the two may be pushed together to expose and open an aperture into which the device 100 or a portion thereof such as the shafts 102, 110 may be inserted.

In some embodiments the device 100 may be configured to integrate with other tools for a variety of purposes, such as integrating with a gynecological speculum to reduce the tenaculum's profile and further improve the visibility through the speculum.

Figure 6:
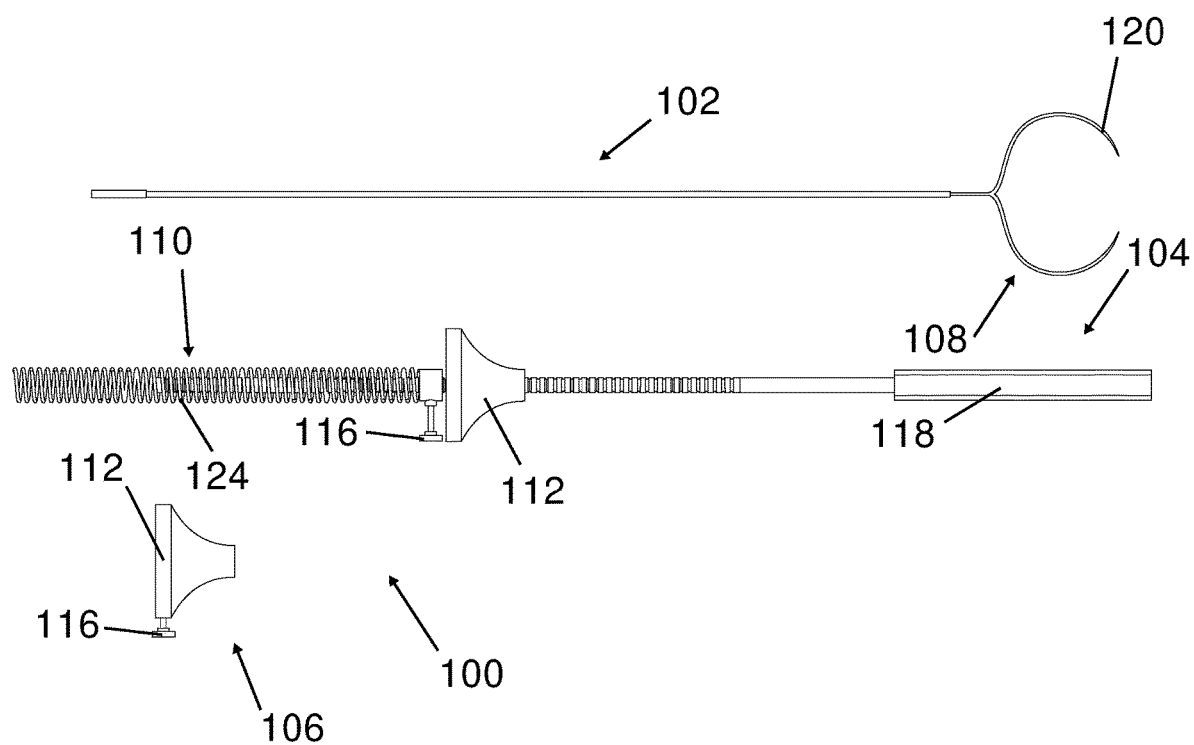
FIG. 6 is a top view of a disassembled cervical tenaculum device, in accordance with an embodiment of the invention.

FIG. 6 is a top view of a disassembled cervical tenaculum device, in accordance with an embodiment of the invention.

In some embodiments, the device 100 comprises a shaft 102 (sometimes called the interior shaft) comprised of a first end 104 and a second end 106; a clamp 108 configured to be locked or unlocked attached to the first end 104 of the shaft; an actuator shaft 110 that is removably coupled to the shaft 102, slidable along the shaft 102, and configured to open and close the clamp 108. In some embodiments, the invention has two or more handles 112 that can be attached along the length of the actuator shaft 110 or shaft 102; in some of these embodiments the portion of the actuator shaft 110 that is between the handles 112 may be comprised of a removably attached coil 124 such that when the handles 112 are pulled towards each other the interior shaft 102 is pressed forward, which operates the clamp 108 such as by opening it or altering its configuration.

Some configurations of the device 100 involve a shaft 102, with a clamp 108 attached at one end, enveloped by the actuator shaft 110 further comprised of a coil 124, with two handles 112 positioned such that one is at the end of the shaft opposite the clamp 108 and the other is at a roughly medial (though it may vary if needed) position along the shaft. The handle 112 near the end of the shaft 102 is attached to the shaft 102, while the handle 112 in the medial position is attached to the actuator shaft 110 at the end of the coil 124, such that when a user presses on the handle 112 at the end of the shaft 102 while holding the handle 112 located at the medial position it pushes the clamp 108 through the actuator shaft 110 and compresses the coil 124 of the actuator shaft 110, which in turn pushes the clamp 108 out of the sheath 118. When the pressure is released, the coil 124 of the actuator shaft 110 extends and the sheath 118 closes the clamp 108.

In some embodiments the device 100 is further comprised of an actuator shaft 110 that may be operated by a twisting movement, push-pull movement, plunger, quick-release screw, or other means of engaging the actuator and in turn the clamp 108. In some embodiments the actuator shaft 110 may have multiple components allowing it to be held in various configurations such as being configured to remove the actuator shaft 110 or portions thereof once the clamp 108 is in place, remove the actuator shaft 110 and shaft 102 entirely once the clamp 108 is in place, or leave the entire device 100 in the patient. In some embodiments, the actuator shaft 110 may further comprise a compressible coil 124 that may be removably attached to the actuator shaft 110 or held on to it by a handle 112 or set screw 116.

In some embodiments, the device 100 is comprised of an internal shaft 102 with at least two ends 104, 106. At one end the clamp 108 may be attached. An external shaft 110, the actuator shaft 110, may envelop the internal shaft 102; in which case it may be a hollow cylindrical shape so that it wraps around the internal shaft 102. The interior or actuator shafts 102, 110 may be at least partially flexible and/or compressible; in some embodiments the actuator shaft 110 may be further comprised of a removably attached coil 124 of material such as, but not limited to, metal or a polymer that may partially envelop the actuator shaft 110. In some embodiments, there may be two handles 112 attached at either end of the actuator shaft 110 in order to attach it to the internal shaft 102; and in some of those embodiments the handles 112 may be attached by screwing onto the internal shaft 102 to keep the external actuator shaft 110 in place, or may be attached by a set-screw 116, clasp, or clamp; in some embodiments the actuator shaft 110 or a portion thereof may be trapped between them or held via pressure from set screws 116 against the interior shaft 102. In some embodiments the clamp 108 is expressed and opened by pressing on the rear handle 112 so that the actuator shaft 110 compresses and in turn pushes the internal shaft 102 forward.

In some embodiments the internal 102 and actuator shafts 110 may be flexible such that they can be bent, allowing a practitioner to attach them to an anchor or other grounding point while also moving them out of the way so that the practitioner can work. In some embodiments, the device 100 may have specific points along the internal 102 and actuator shafts 110 where the bending occurs, while in other embodiments the full length of the shaft 102, 110 components may be flexible. The internal or actuator shafts 102, 110 may have threading in some embodiments that is configured to receive one or more handles 112; in other embodiments the handles 112 attach via set-screws 116 that place press the handle into the shaft. The shafts may be substantially cylindrical, flat, or other shapes. In at least one embodiment the shafts 102, 110 are substantially cylindrical and the interior shaft 102 is able to rotate within the actuator shaft 110, though in various embodiments there may be pressures preventing free rotation such as pressure applying the handle 112 to the shaft 102 via the set screw 116, or a close fit from the actuator shaft 110. In some embodiments the shafts 102, 110 are substantially straight, while in others one or both shafts 102 110 may be curved or bent to enable specialized manipulation of tissue or articles.

In some embodiments, a practitioner or user engages the device by pressing on the actuator shaft 110 while pulling back on the shaft 102 or a handle 112 on the shaft 102, which in turn causes the clamp 108 to open. Some examples involve a sheath 118 attached to the actuator shaft 110 and overlapping the clamp 108 that fully covers it when the actuator shaft 110 is not being utilized, but when a user presses the handles 112 together it pushes the clamp 108 out of the sheath 118 which allows the clamp 108 to open; in such embodiments the clamp 108 may favor an opened position instead of closed or may even be a single piece of material which was constructed in an open position. Some embodiments may include a coil 124 between the handles 112 and at least partially enveloping the actuator shaft 110 to apply an opening pressure. The tips 120 of the clamp 108 can then be applied to a cervix or other article to be held, and once it is in a location the practitioner deems appropriate the actuator shaft 110 and handle(s) 112 can be released, which relieves the pressure keeping the clamp 108 open and closes the clamp 108, thereby taking hold of the article. The device 100 is then free to remain in the patient and grasping the article while the practitioner works utilizing other tools.

In some embodiments the clamp 108 is a jawed-clamp or other configuration wherein the clamp 108 may automatically favor a closed position over an open one and exerts tension on the points or pressure exerting areas of the clamp's tips 120. Some examples may have a complex clamp 108 structure wherein the clamp 108 has multiple modes that can be operated through the actuator shaft 110 and/or handles 112; such as locking the clamp 108 in its current position by twisting a handle 112 at a certain point, or it may have a click-in mechanism allowing it to hold pressure that can be quickly released. In some embodiments, the clamp 108 has a mechanism such as a screw, ratchet, or other variable tension means to place tension on the grasping means. In some embodiments the clamp 108 may be constructed as a single component wherein a piece of material, possibly a metal, is split and forked so that two tines are created, then bent towards each other, leaving a gap between them as necessary for the user, such that when the tines are pressed towards each other the tips 120 close the gap. In some embodiments, the tips 120 may contact each other, while in other embodiments they may overlap or pass each other. In some embodiments the mechanism is in the form of pointed tips 120 such as found in a common surgical tenaculum, or may be rounded, while in other embodiments it may involve a shaped pad or rod allowing it to displace the force over the surface it is grasping and diminish any trauma to the area or article being grasped. In some embodiments the clamp 108 may be a tether that encircles the area to be held like a noose or similar means. In some embodiments the clamp 108 is a pinch-based grasping means with two prongs, while in others it may have additional prongs as needed to sufficiently grasp and hold the article in question. In some embodiments, the clamp 108 is comprised of one or more hinges pivoted together such that when tension is placed on corresponding ends of the hinges the opposite ends are closed. In some embodiments, the clamp 108 is comprised of one or more hinges, such as scissor-hinges, that are connected with each other and operable against each other such that operating one hinge will operate another. In some embodiments the clamp 108 may be locked into position such that it does not exert any additional pressure once they are locked or closed to a certain degree; in other embodiments they may exert continuous closing or opening pressure. In some embodiment the clamp 108 may be at least partially flexible.

In some embodiments, the clamp 108 does not automatically favor a closed position but may favor a neutral or open position. Examples of such may feature a clamp 108 that is comprised of a single piece of material or it may have a spring integrated into the jaws of the clamp 108 that pushes it open. In some embodiments, the clamp 108 is also a scissors-style hinge mechanism wherein a distal end is designed to be a grasping end while a proximal end is the end engaged by the actuator shaft 110. In some embodiments, the clamp 108 may have a quick-release mechanism, retrieval cord, or other means of disengaging tension. In some embodiments, the scissors-style hinge clamp 108 may have a means of disengaging tension including a latch, catch, screw, and/or may be pushed on by the tether in order to release the tension.

In some embodiments the entire device 100 is disposable, while in others it is designed to be reused. In some embodiments certain components are disposable while other components in the same embodiment may be reusable. In some embodiments, the components of the device 100 may be comprised of one or more substances from the list including, but not limited to, silicone, plastic, metal, composites, or combinations thereof.

In some embodiments, the device 100 is further comprised of an anchor that is comprised of a securing mechanism configured to be attached to a speculum or other surgical instrument or may be configured to adhere to skin or other surfaces and may be configured to hold the shafts 102, 110 or tether. The securing mechanism may be, but is not limited to, a mechanical clip, an adhesive patch, a pin, a needle to thread through a medium, a screw, an aperture through which the shafts 102, 110 of the device 100 can be threaded (or said aperture can be opened to allow the shaft to be threaded) and/or a clasp. The securing mechanism may alternatively be a combination of the aforementioned components configured in a complementary way. For some examples of the device 100, the anchor includes a thread, hole, notch, clasp, or other means to secure the shaft or tether to the anchor, allowing the anchor to hold tension on the shaft or tether and by extension the article that the clasp is holding. In some embodiments, the anchor is configured to attach to a range of other surgical stabilizers or instruments including, but not limited to, a speculum. For some embodiments, the anchor is comprised in part of two overlapping cylinders wherein the two may be pushed together to expose and open an aperture into which the device 100 or a portion thereof such as the shafts 102, 110 may be inserted.

In some embodiments the device 100 may be configured to integrate with other tools for a variety of purposes, such as integrating with a gynecological speculum to reduce the tenaculum's profile and further improve the visibility through the speculum.

Figure 7:
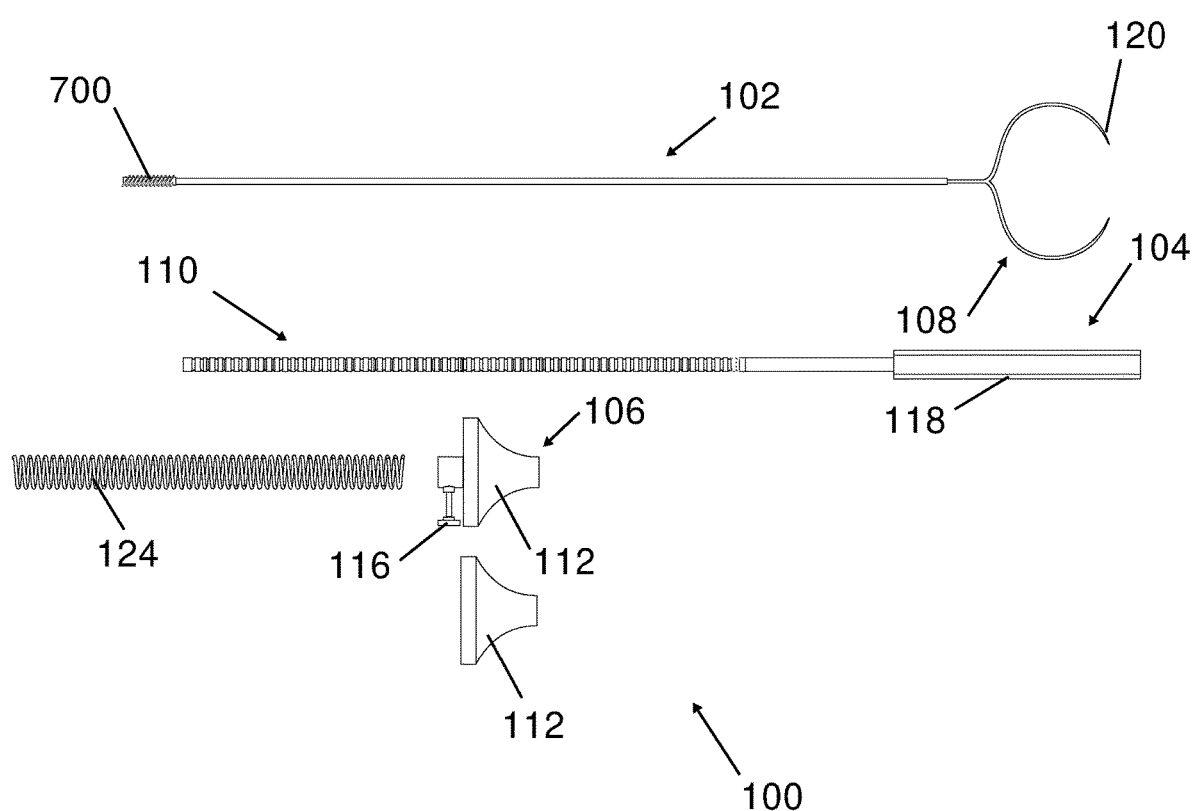
FIG. 7 is a top view of a disassembled cervical tenaculum device, in accordance with an embodiment of the invention.

FIG. 7 is a top view of a disassembled cervical tenaculum device, in accordance with an embodiment of the invention.

In some embodiments, the device 100 comprises a shaft 102 (sometimes called the interior shaft) comprised of a first end 104 and a second end 106; a clamp 108 configured to be locked or unlocked attached to the first end 104 of the shaft; an actuator shaft 110 that is removably coupled to the shaft 102, slidable along the shaft 102, and configured to open and close the clamp 108. In some embodiments, the invention has two or more handles 112 that can be attached along the length of the actuator shaft 110 or shaft 102; in some of these embodiments the portion of the actuator shaft 110 that is between the handles 112 may be comprised of a removably attached coil 124 such that when the handles 112 are pulled towards each other the interior shaft 102 is pressed forward, which operates the clamp 108 such as by opening it or altering its configuration.

Some configurations of the device 100 involve a shaft 102, with a clamp 108 attached at one end, enveloped by the actuator shaft 110 further comprised of a coil 124, with two handles 112 positioned such that one is at the end of the shaft opposite the clamp 108 and the other is at a roughly medial (though it may vary if needed) position along the shaft. The handle 112 near the end of the shaft 102 is attached to the shaft 102, while the handle 112 in the medial position is attached to the actuator shaft 110 at the end of the coil 124, such that when a user presses on the handle 112 at the end of the shaft 102 while holding the handle 112 located at the medial position it pushes the clamp 108 through the actuator shaft 110 and compresses the coil 124 of the actuator shaft 110, which in turn pushes the clamp 108 out of the sheath 118. When the pressure is released, the coil 124 of the actuator shaft 110 extends and the sheath 118 closes the clamp 108.

In some embodiments the device 100 is further comprised of an actuator shaft 110 that may be operated by a twisting movement, push-pull movement, plunger, quick-release screw, or other means of engaging the actuator and in turn the clamp 108. In some embodiments the actuator shaft 110 may have multiple components allowing it to be held in various configurations such as being configured to remove the actuator shaft 110 or portions thereof once the clamp 108 is in place, remove the actuator shaft 110 and shaft 102 entirely once the clamp 108 is in place, or leave the entire device 100 in the patient. In some embodiments, the actuator shaft 110 may further comprise a compressible coil 124 that may be removably attached to the actuator shaft 110 or held on to it by a handle 112 or set screw 116.

In some embodiments, the device 100 is comprised of an internal shaft 102 with at least two ends 104, 106. At one end the clamp 108 may be attached. An external shaft 110, the actuator shaft 110, may envelop the internal shaft 102; in which case it may be a hollow cylindrical shape so that it wraps around the internal shaft 102. The interior or actuator shafts 102, 110 may be at least partially flexible and/or compressible; in some embodiments the actuator shaft 110 may be further comprised of a removably attached coil 124 of material such as, but not limited to, metal or a polymer that may partially envelop the actuator shaft 110. In some embodiments, there may be two handles 112 attached at either end of the actuator shaft 110 in order to attach it to the internal shaft 102; and in some of those embodiments the handles 112 may be attached by screwing onto the internal shaft 102 to keep the external actuator shaft 110 in place, or may be attached by a set-screw 116, clasp, or clamp; in some embodiments the actuator shaft 110 or a portion thereof may be trapped between them or held via pressure from set screws 116 against the interior shaft 102. In some embodiments the clamp 108 is expressed and opened by pressing on the rear handle 112 so that the actuator shaft 110 compresses and in turn pushes the internal shaft 102 forward.

In some embodiments the internal 102 and actuator shafts 110 may be flexible such that they can be bent, allowing a practitioner to attach them to an anchor or other grounding point while also moving them out of the way so that the practitioner can work. In some embodiments, the device 100 may have specific points along the internal 102 and actuator shafts 110 where the bending occurs, while in other embodiments the full length of the shaft 102, 110 components may be flexible. The internal or actuator shafts 102, 110 may have threading 700 in some embodiments that is configured to receive one or more handles 112 which may also be threaded to receive the threading 700; in other embodiments the handles 112 attach via set-screws 116 that place press the handle into the shaft. The shafts may be substantially cylindrical, flat, or other shapes. In at least one embodiment the shafts 102, 110 are substantially cylindrical and the interior shaft 102 is able to rotate within the actuator shaft 110, though in various embodiments there may be pressures preventing free rotation such as pressure applying the handle 112 to the shaft 102 via the set screw 116, or a close fit from the actuator shaft 110. In some embodiments the shafts 102, 110 are substantially straight, while in others one or both shafts 102 110 may be curved or bent to enable specialized manipulation of tissue or articles.

In some embodiments, a practitioner or user engages the device by pressing on the actuator shaft 110 while pulling back on the shaft 102 or a handle 112 on the shaft 102, which in turn causes the clamp 108 to open. Some examples involve a sheath 118 attached to the actuator shaft 110 and overlapping the clamp 108 that fully covers it when the actuator shaft 110 is not being utilized, but when a user presses the handles 112 together it pushes the clamp 108 out of the sheath 118 which allows the clamp 108 to open; in such embodiments the clamp 108 may favor an opened position instead of closed or may even be a single piece of material which was constructed in an open position. Some embodiments may include a coil 124 between the handles 112 and at least partially enveloping the actuator shaft 110 to apply an opening pressure. The tips 120 of the clamp can then be applied to a cervix or other article to be held, and once it is in a location the practitioner deems appropriate the actuator shaft 110 and handle(s) 112 can be released, which relieves the pressure keeping the clamp 108 open and closes the clamp 108, thereby taking hold of the article. The device 100 is then free to remain in the patient and grasping the article while the practitioner works utilizing other tools.

In some embodiments the clamp 108 is a jawed-clamp or other configuration wherein the clamp 108 may automatically favor a closed position over an open one and exerts tension on the points or pressure exerting areas of the clamp's tips 120. Some examples may have a complex clamp 108 structure wherein the clamp 108 has multiple modes that can be operated through the actuator shaft 110 and/or handles 112; such as locking the clamp 108 in its current position by twisting a handle 112 at a certain point, or it may have a click-in mechanism allowing it to hold pressure that can be quickly released. In some embodiments, the clamp 108 has a mechanism such as a screw, ratchet, or other variable tension means to place tension on the grasping means. In some embodiments the clamp 108 may be constructed as a single component wherein a piece of material, possibly a metal, is split and forked so that two tines are created, then bent towards each other, leaving a gap between them as necessary for the user, such that when the tines are pressed towards each other the tips 120 close the gap. In some embodiments, the tips 120 may contact each other, while in other embodiments they may overlap or pass each other. In some embodiments the mechanism is in the form of pointed tips 120 such as found in a common surgical tenaculum, or may be rounded, while in other embodiments it may involve a shaped pad or rod allowing it to displace the force over the surface it is grasping and diminish any trauma to the area or article being grasped. In some embodiments the clamp 108 may be a tether that encircles the area to be held like a noose or similar means. In some embodiments the clamp 108 is a pinch-based grasping means with two prongs, while in others it may have additional prongs as needed to sufficiently grasp and hold the article in question. In some embodiments, the clamp 108 is comprised of one or more hinges pivoted together such that when tension is placed on corresponding ends of the hinges the opposite ends are closed. In some embodiments, the clamp 108 is comprised of one or more hinges, such as scissor-hinges, that are connected with each other and operable against each other such that operating one hinge will operate another. In some embodiments the clamp 108 may be locked into position such that it does not exert any additional pressure once they are locked or closed to a certain degree; in other embodiments they may exert continuous closing or opening pressure. In some embodiment the clamp 108 may be at least partially flexible.

In some embodiments, the clamp 108 does not automatically favor a closed position but may favor a neutral or open position. Examples of such may feature a clamp 108 that is comprised of a single piece of material or it may have a spring integrated into the jaws of the clamp 108 that pushes it open. In some embodiments, the clamp 108 is also a scissors-style hinge mechanism wherein a distal end is designed to be a grasping end while a proximal end is the end engaged by the actuator shaft 110. In some embodiments, the clamp 108 may have a quick-release mechanism, retrieval cord, or other means of disengaging tension. In some embodiments, the scissors-style hinge clamp 108 may have a means of disengaging tension including a latch, catch, screw, and/or may be pushed on by the tether in order to release the tension.

In some embodiments the entire device 100 is disposable, while in others it is designed to be reused. In some embodiments certain components are disposable while other components in the same embodiment may be reusable. In some embodiments, the components of the device 100 may be comprised of one or more substances from the list including, but not limited to, silicone, plastic, metal, composites, or combinations thereof.

In some embodiments, the device 100 is further comprised of an anchor that is comprised of a securing mechanism configured to be attached to a speculum or other surgical instrument or may be configured to adhere to skin or other surfaces and may be configured to hold the shafts 102, 110 or tether. The securing mechanism may be, but is not limited to, a mechanical clip, an adhesive patch, a pin, a needle to thread through a medium, a screw, an aperture through which the shafts 102, 110 of the device 100 can be threaded (or said aperture can be opened to allow the shaft to be threaded) and/or a clasp. The securing mechanism may alternatively be a combination of the aforementioned components configured in a complementary way. For some examples of the device 100, the anchor includes a thread, hole, notch, clasp, or other means to secure the shaft or tether to the anchor, allowing the anchor to hold tension on the shaft or tether and by extension the article that the clasp is holding. In some embodiments, the anchor is configured to attach to a range of other surgical stabilizers or instruments including, but not limited to, a speculum. For some embodiments, the anchor is comprised in part of two overlapping cylinders wherein the two may be pushed together to expose and open an aperture into which the device 100 or a portion thereof such as the shafts 102, 110 may be inserted.

In some embodiments the device 100 may be configured to integrate with other tools for a variety of purposes, such as integrating with a gynecological speculum to reduce the tenaculum's profile and further improve the visibility through the speculum.

Figure 8:
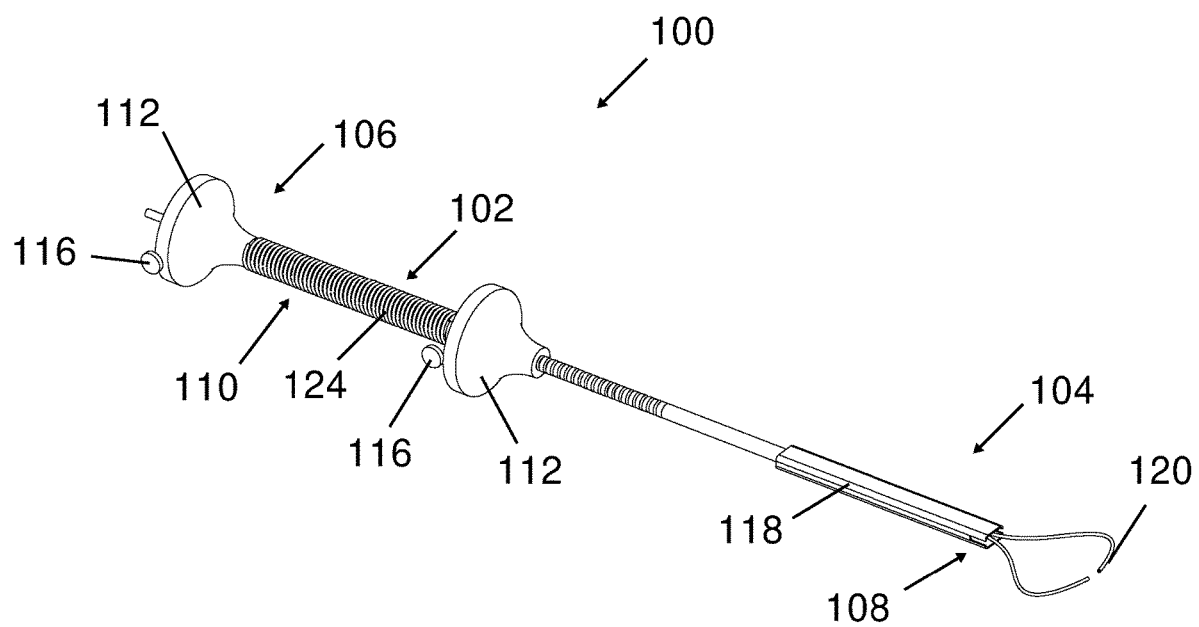
FIG. 8 is a perspective view of a cervical tenaculum device, in accordance with an embodiment of the invention.

FIG. 8 is a perspective view of a cervical tenaculum device, in accordance with an embodiment of the invention.

In some embodiments, the device 100 comprises a shaft 102 (sometimes called the interior shaft) comprised of a first end 104 and a second end 106; a clamp 108 configured to be locked or unlocked attached to the first end 104 of the shaft; an actuator shaft 110 that is removably coupled to the shaft 102, slidable along the shaft 102, and configured to open and close the clamp 108. In some embodiments, the invention has two or more handles 112 that can be attached along the length of the actuator shaft 110 or shaft 102; in some of these embodiments the portion of the actuator shaft 110 that is between the handles 112 may be comprised of a removably attached coil 124 such that when the handles 112 are pulled towards each other the interior shaft 102 is pressed forward, which operates the clamp 108 such as by opening it or altering its configuration.

Some configurations of the device 100 involve a shaft 102, with a clamp 108 attached at one end, enveloped by the actuator shaft 110 further comprised of a coil 124, with two handles 112 positioned such that one is at the end of the shaft opposite the clamp 108 and the other is at a roughly medial (though it may vary if needed) position along the shaft. The handle 112 near the end of the shaft 102 is attached to the shaft 102, while the handle 112 in the medial position is attached to the actuator shaft 110 at the end of the coil 124, such that when a user presses on the handle 112 at the end of the shaft 102 while holding the handle 112 located at the medial position it pushes the clamp 108 through the actuator shaft 110 and compresses the coil 124 of the actuator shaft 110, which in turn pushes the clamp 108 out of the sheath 118 as depicted in FIG. 8. When the pressure is released, the coil 124 of the actuator shaft 110 extends and the sheath 118 closes the clamp 108.

In some embodiments the device 100 is further comprised of an actuator shaft 110 that may be operated by a twisting movement, push-pull movement, plunger, quick-release screw, or other means of engaging the actuator and in turn the clamp 108. In some embodiments the actuator shaft 110 may have multiple components allowing it to be held in various configurations such as being configured to remove the actuator shaft 110 or portions thereof once the clamp 108 is in place, remove the actuator shaft 110 and shaft 102 entirely once the clamp 108 is in place, or leave the entire device 100 in the patient. In some embodiments, the actuator shaft 110 may further comprise a compressible coil 124 that may be removably attached to the actuator shaft 110 or held on to it by a handle 112 or set screw 116.

In some embodiments, the device 100 is comprised of an internal shaft 102 with at least two ends 104, 106. At one end the clamp 108 may be attached. An external shaft 110, the actuator shaft 110, may envelop the internal shaft 102; in which case it may be a hollow cylindrical shape so that it wraps around the internal shaft 102. The interior or actuator shafts 102, 110 may be at least partially flexible and/or compressible; in some embodiments the actuator shaft 110 may be further comprised of a removably attached coil 124 of material such as, but not limited to, metal or a polymer that may partially envelop the actuator shaft 110. In some embodiments, there may be two handles 112 attached at either end of the actuator shaft 110 in order to attach it to the internal shaft 102; and in some of those embodiments the handles 112 may be attached by screwing onto the internal shaft 102 to keep the external actuator shaft 110 in place, or may be attached by a set-screw 116, clasp, or clamp; in some embodiments the actuator shaft 110 or a portion thereof may be trapped between them or held via pressure from set screws 116 against the interior shaft 102. In some embodiments the clamp 108 is expressed and opened by pressing on the rear handle 112 so that the actuator shaft 110 compresses and in turn pushes the internal shaft 102 forward.

In some embodiments the internal 102 and actuator shafts 110 may be flexible such that they can be bent, allowing a practitioner to attach them to an anchor or other grounding point while also moving them out of the way so that the practitioner can work. In some embodiments, the device 100 may have specific points along the internal 102 and actuator shafts 110 where the bending occurs, while in other embodiments the full length of the shaft 102, 110 components may be flexible. The internal or actuator shafts 102, 110 may have threading in some embodiments that is configured to receive one or more handles 112; in other embodiments the handles 112 attach via set-screws 116 that place press the handle into the shaft. The shafts may be substantially cylindrical, flat, or other shapes. In at least one embodiment the shafts 102, 110 are substantially cylindrical and the interior shaft 102 is able to rotate within the actuator shaft 110, though in various embodiments there may be pressures preventing free rotation such as pressure applying the handle 112 to the shaft 102 via the set screw 116, or a close fit from the actuator shaft 110. In some embodiments the shafts 102, 110 are substantially straight, while in others one or both shafts 102 110 may be curved or bent to enable specialized manipulation of tissue or articles.

In some embodiments, a practitioner or user engages the device by pressing on the actuator shaft 110 while pulling back on the shaft 102 or a handle 112 on the shaft 102, which in turn causes the clamp 108 to open. Some examples involve a sheath 118 attached to the actuator shaft 110 and overlapping the clamp 108 that fully covers it when the actuator shaft 110 is not being utilized, but when a user presses the handles 112 together it pushes the clamp 108 out of the sheath 118 which allows the clamp 108 to open; in such embodiments the clamp 108 may favor an opened position instead of closed or may even be a single piece of material which was constructed in an open position. Some embodiments may include a coil 124 between the handles 112 and at least partially enveloping the actuator shaft 110 to apply an opening pressure. The tips 120 of the clamp 108 can then be applied to a cervix or other article to be held, and once it is in a location the practitioner deems appropriate the actuator shaft 110 and handle(s) 112 can be released, which relieves the pressure keeping the clamp 108 open and closes the clamp 108, thereby taking hold of the article. The device 100 is then free to remain in the patient and grasping the article while the practitioner works utilizing other tools.

In some embodiments the clamp 108 is a jawed-clamp or other configuration wherein the clamp 108 may automatically favor a closed position over an open one and exerts tension on the points or pressure exerting areas of the clamp's tips 120. Some examples may have a complex clamp 108 structure wherein the clamp 108 has multiple modes that can be operated through the actuator shaft 110 and/or handles 112; such as locking the clamp 108 in its current position by twisting a handle 112 at a certain point, or it may have a click-in mechanism allowing it to hold pressure that can be quickly released. In some embodiments, the clamp 108 has a mechanism such as a screw, ratchet, or other variable tension means to place tension on the grasping means. In some embodiments the clamp 108 may be constructed as a single component wherein a piece of material, possibly a metal, is split and forked so that two tines are created, then bent towards each other, leaving a gap between them as necessary for the user, such that when the tines are pressed towards each other the tips 120 close the gap. In some embodiments, the tips 120 may contact each other, while in other embodiments they may overlap or pass each other. In some embodiments the mechanism is in the form of pointed tips 120 such as found in a common surgical tenaculum, or may be rounded, while in other embodiments it may involve a shaped pad or rod allowing it to displace the force over the surface it is grasping and diminish any trauma to the area or article being grasped. In some embodiments the clamp 108 may be a tether that encircles the area to be held like a noose or similar means. In some embodiments the clamp 108 is a pinch-based grasping means with two prongs, while in others it may have additional prongs as needed to sufficiently grasp and hold the article in question. In some embodiments, the clamp 108 is comprised of one or more hinges pivoted together such that when tension is placed on corresponding ends of the hinges the opposite ends are closed. In some embodiments, the clamp 108 is comprised of one or more hinges, such as scissor-hinges, that are connected with each other and operable against each other such that operating one hinge will operate another. In some embodiments the clamp 108 may be locked into position such that it does not exert any additional pressure once they are locked or closed to a certain degree; in other embodiments they may exert continuous closing or opening pressure. In some embodiment the clamp 108 may be at least partially flexible.

In some embodiments, the clamp 108 does not automatically favor a closed position but may favor a neutral or open position. Examples of such may feature a clamp 108 that is comprised of a single piece of material or it may have a spring integrated into the jaws of the clamp 108 that pushes it open. In some embodiments, the clamp 108 is also a scissors-style hinge mechanism wherein a distal end is designed to be a grasping end while a proximal end is the end engaged by the actuator shaft 110. In some embodiments, the clamp 108 may have a quick-release mechanism, retrieval cord, or other means of disengaging tension. In some embodiments, the scissors-style hinge clamp 108 may have a means of disengaging tension including a latch, catch, screw, and/or may be pushed on by the tether in order to release the tension.

In some embodiments the entire device 100 is disposable, while in others it is designed to be reused. In some embodiments certain components are disposable while other components in the same embodiment may be reusable. In some embodiments, the components of the device 100 may be comprised of one or more substances from the list including, but not limited to, silicone, plastic, metal, composites, or combinations thereof.

In some embodiments, the device 100 is further comprised of an anchor that is comprised of a securing mechanism configured to be attached to a speculum or other surgical instrument or may be configured to adhere to skin or other surfaces and may be configured to hold the shafts 102, 110 or tether. The securing mechanism may be, but is not limited to, a mechanical clip, an adhesive patch, a pin, a needle to thread through a medium, a screw, an aperture through which the shafts 102, 110 of the device 100 can be threaded (or said aperture can be opened to allow the shaft to be threaded) and/or a clasp. The securing mechanism may alternatively be a combination of the aforementioned components configured in a complementary way. For some examples of the device 100, the anchor includes a thread, hole, notch, clasp, or other means to secure the shaft or tether to the anchor, allowing the anchor to hold tension on the shaft or tether and by extension the article that the clasp is holding. In some embodiments, the anchor is configured to attach to a range of other surgical stabilizers or instruments including, but not limited to, a speculum. For some embodiments, the anchor is comprised in part of two overlapping cylinders wherein the two may be pushed together to expose and open an aperture into which the device 100 or a portion thereof such as the shafts 102, 110 may be inserted.

In some embodiments the device 100 may be configured to integrate with other tools for a variety of purposes, such as integrating with a gynecological speculum to reduce the tenaculum's profile and further improve the visibility through the speculum.

Figure 9:
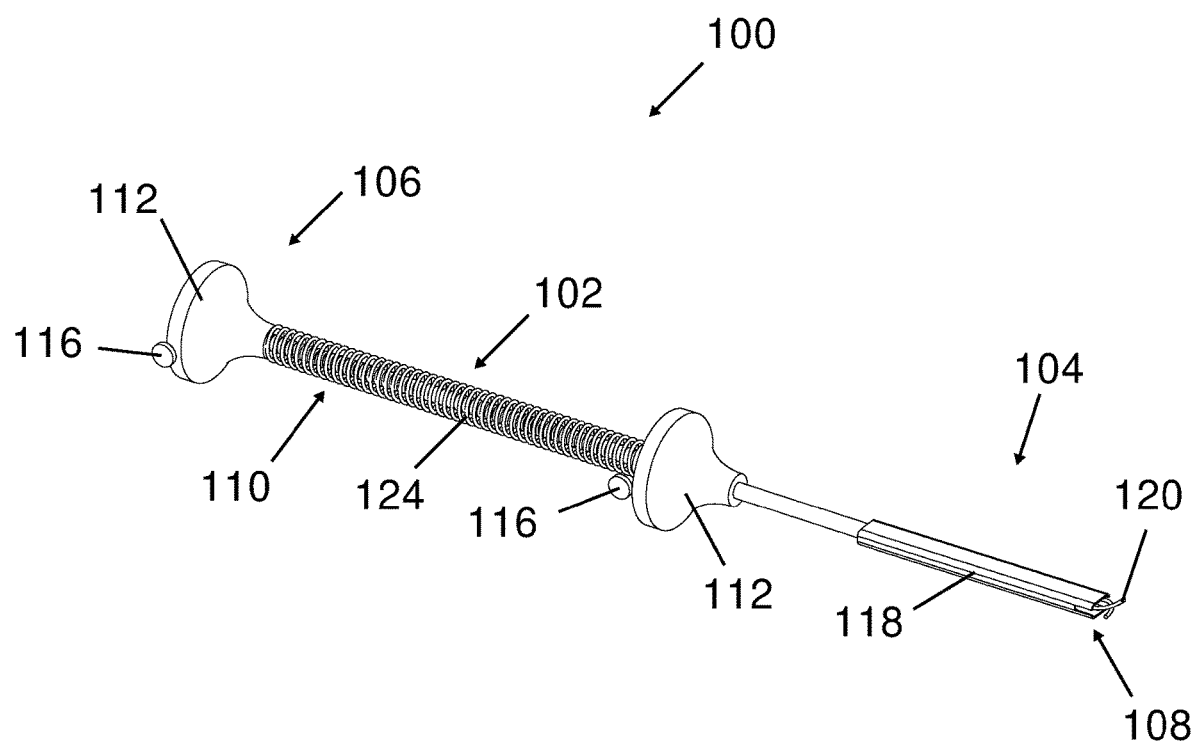
FIG. 9 is a perspective view of a cervical tenaculum device, in accordance with an embodiment of the invention.

FIG. 9 is a perspective view of a cervical tenaculum device, in accordance with an embodiment of the invention.

In some embodiments, the device 100 comprises a shaft 102 (sometimes called the interior shaft) comprised of a first end 104 and a second end 106; a clamp 108 configured to be locked or unlocked attached to the first end 104 of the shaft; an actuator shaft 110 that is removably coupled to the shaft 102, slidable along the shaft 102, and configured to open and close the clamp 108. In some embodiments, the invention has two or more handles 112 that can be attached along the length of the actuator shaft 110 or shaft 102; in some of these embodiments the portion of the actuator shaft 110 that is between the handles 112 may be comprised of a removably attached coil 124 such that when the handles 112 are pulled towards each other the interior shaft 102 is pressed forward, which operates the clamp 108 such as by opening it or altering its configuration.

Some configurations of the device 100 involve a shaft 102, with a clamp 108 attached at one end, enveloped by the actuator shaft 110 further comprised of a coil 124, with two handles 112 positioned such that one is at the end of the shaft opposite the clamp 108 and the other is at a roughly medial (though it may vary if needed) position along the shaft. The handle 112 near the end of the shaft 102 is attached to the shaft 102, while the handle 112 in the medial position is attached to the actuator shaft 110 at the end of the coil 124, such that when a user presses on the handle 112 at the end of the shaft 102 while holding the handle 112 located at the medial position it pushes the clamp 108 through the actuator shaft 110 and compresses the coil 124 of the actuator shaft 110, which in turn pushes the clamp 108 out of the sheath 118 as depicted in FIG. 8. When the pressure is released, the coil 124 of the actuator shaft 110 extends and the sheath 118 closes the clamp 108.

In some embodiments the device 100 is further comprised of an actuator shaft 110 that may be operated by a twisting movement, push-pull movement, plunger, quick-release screw, or other means of engaging the actuator and in turn the clamp 108. In some embodiments the actuator shaft 110 may have multiple components allowing it to be held in various configurations such as being configured to remove the actuator shaft 110 or portions thereof once the clamp 108 is in place, remove the actuator shaft 110 and shaft 102 entirely once the clamp 108 is in place, or leave the entire device 100 in the patient. In some embodiments, the actuator shaft 110 may further comprise a compressible coil 124 that may be removably attached to the actuator shaft 110 or held on to it by a handle 112 or set screw 116.

In some embodiments, the device 100 is comprised of an internal shaft 102 with at least two ends 104, 106. At one end the clamp 108 may be attached. An external shaft 110, the actuator shaft 110, may envelop the internal shaft 102; in which case it may be a hollow cylindrical shape so that it wraps around the internal shaft 102. The interior or actuator shafts 102, 110 may be at least partially flexible and/or compressible; in some embodiments the actuator shaft 110 may be further comprised of a removably attached coil 124 of material such as, but not limited to, metal or a polymer that may partially envelop the actuator shaft 110. In some embodiments, there may be two handles 112 attached at either end of the actuator shaft 110 in order to attach it to the internal shaft 102; and in some of those embodiments the handles 112 may be attached by screwing onto the internal shaft 102 to keep the external actuator shaft 110 in place, or may be attached by a set-screw 116, clasp, or clamp; in some embodiments the actuator shaft 110 or a portion thereof may be trapped between them or held via pressure from set screws 116 against the interior shaft 102. In some embodiments the clamp 108 is expressed and opened by pressing on the rear handle 112 so that the actuator shaft 110 compresses and in turn pushes the internal shaft 102 forward.

In some embodiments the internal 102 and actuator shafts 110 may be flexible such that they can be bent, allowing a practitioner to attach them to an anchor or other grounding point while also moving them out of the way so that the practitioner can work. In some embodiments, the device 100 may have specific points along the internal 102 and actuator shafts 110 where the bending occurs, while in other embodiments the full length of the shaft 102, 110 components may be flexible. The internal or actuator shafts 102, 110 may have threading in some embodiments that is configured to receive one or more handles 112; in other embodiments the handles 112 attach via set-screws 116 that place press the handle into the shaft. The shafts may be substantially cylindrical, flat, or other shapes. In at least one embodiment the shafts 102, 110 are substantially cylindrical and the interior shaft 102 is able to rotate within the actuator shaft 110, though in various embodiments there may be pressures preventing free rotation such as pressure applying the handle 112 to the shaft 102 via the set screw 116, or a close fit from the actuator shaft 110. In some embodiments the shafts 102, 110 are substantially straight, while in others one or both shafts 102 110 may be curved or bent to enable specialized manipulation of tissue or articles.

In some embodiments, a practitioner or user engages the device by pressing on the actuator shaft 110 while pulling back on the shaft 102 or a handle 112 on the shaft 102, which in turn causes the clamp 108 to open. Some examples involve a sheath 118 attached to the actuator shaft 110 and overlapping the clamp 108 that fully covers it when the actuator shaft 110 is not being utilized, but when a user presses the handles 112 together it pushes the clamp 108 out of the sheath 118 which allows the clamp 108 to open; in such embodiments the clamp 108 may favor an opened position instead of closed or may even be a single piece of material which was constructed in an open position. Some embodiments may include a coil 124 between the handles 112 and at least partially enveloping the actuator shaft 110 to apply an opening pressure. The tips 120 of the clamp 108 can then be applied to a cervix or other article to be held, and once it is in a location the practitioner deems appropriate the actuator shaft 110 and handle(s) 112 can be released, which relieves the pressure keeping the clamp 108 open and closes the clamp 108, thereby taking hold of the article. The device 100 is then free to remain in the patient and grasping the article while the practitioner works utilizing other tools.

In some embodiments the clamp 108 is a jawed-clamp or other configuration wherein the clamp 108 may automatically favor a closed position over an open one and exerts tension on the points or pressure exerting areas of the clamp's tips 120. Some examples may have a complex clamp 108 structure wherein the clamp 108 has multiple modes that can be operated through the actuator shaft 110 and/or handles 112; such as locking the clamp 108 in its current position by twisting a handle 112 at a certain point, or it may have a click-in mechanism allowing it to hold pressure that can be quickly released. In some embodiments, the clamp 108 has a mechanism such as a screw, ratchet, or other variable tension means to place tension on the grasping means. In some embodiments the clamp 108 may be constructed as a single component wherein a piece of material, possibly a metal, is split and forked so that two tines are created, then bent towards each other, leaving a gap between them as necessary for the user, such that when the tines are pressed towards each other the tips 120 close the gap. In some embodiments, the tips 120 may contact each other, while in other embodiments they may overlap or pass each other. In some embodiments the mechanism is in the form of pointed tips 120 such as found in a common surgical tenaculum, or may be rounded, while in other embodiments it may involve a shaped pad or rod allowing it to displace the force over the surface it is grasping and diminish any trauma to the area or article being grasped. In some embodiments the clamp 108 may be a tether that encircles the area to be held like a noose or similar means. In some embodiments the clamp 108 is a pinch-based grasping means with two prongs, while in others it may have additional prongs as needed to sufficiently grasp and hold the article in question. In some embodiments, the clamp 108 is comprised of one or more hinges pivoted together such that when tension is placed on corresponding ends of the hinges the opposite ends are closed. In some embodiments, the clamp 108 is comprised of one or more hinges, such as scissor-hinges, that are connected with each other and operable against each other such that operating one hinge will operate another. In some embodiments the clamp 108 may be locked into position such that it does not exert any additional pressure once they are locked or closed to a certain degree; in other embodiments they may exert continuous closing or opening pressure. In some embodiment the clamp may be at least partially flexible.

In some embodiments, the clamp 108 does not automatically favor a closed position but may favor a neutral or open position. Examples of such may feature a clamp 108 that is comprised of a single piece of material or it may have a spring integrated into the jaws of the clamp 108 that pushes it open. In some embodiments, the clamp 108 is also a scissors-style hinge mechanism wherein a distal end is designed to be a grasping end while a proximal end is the end engaged by the actuator shaft 110. In some embodiments, the clamp 108 may have a quick-release mechanism, retrieval cord, or other means of disengaging tension. In some embodiments, the scissors-style hinge clamp 108 may have a means of disengaging tension including a latch, catch, screw, and/or may be pushed on by the tether in order to release the tension.

In some embodiments the entire device 100 is disposable, while in others it is designed to be reused. In some embodiments certain components are disposable while other components in the same embodiment may be reusable. In some embodiments, the components of the device 100 may be comprised of one or more substances from the list including, but not limited to, silicone, plastic, metal, composites, or combinations thereof.

In some embodiments, the device 100 is further comprised of an anchor that is comprised of a securing mechanism configured to be attached to a speculum or other surgical instrument or may be configured to adhere to skin or other surfaces and may be configured to hold the shafts 102, 110 or tether. The securing mechanism may be, but is not limited to, a mechanical clip, an adhesive patch, a pin, a needle to thread through a medium, a screw, an aperture through which the shafts 102, 110 of the device 100 can be threaded (or said aperture can be opened to allow the shaft to be threaded) and/or a clasp. The securing mechanism may alternatively be a combination of the aforementioned components configured in a complementary way. For some examples of the device 100, the anchor includes a thread, hole, notch, clasp, or other means to secure the shaft or tether to the anchor, allowing the anchor to hold tension on the shaft or tether and by extension the article that the clasp is holding. In some embodiments, the anchor is configured to attach to a range of other surgical stabilizers or instruments including, but not limited to, a speculum. For some embodiments, the anchor is comprised in part of two overlapping cylinders wherein the two may be pushed together to expose and open an aperture into which the device 100 or a portion thereof such as the shafts 102, 110 may be inserted.

In some embodiments the device 100 may be configured to integrate with other tools for a variety of purposes, such as integrating with a gynecological speculum to reduce the tenaculum's profile and further improve the visibility through the speculum.

Figure 10:
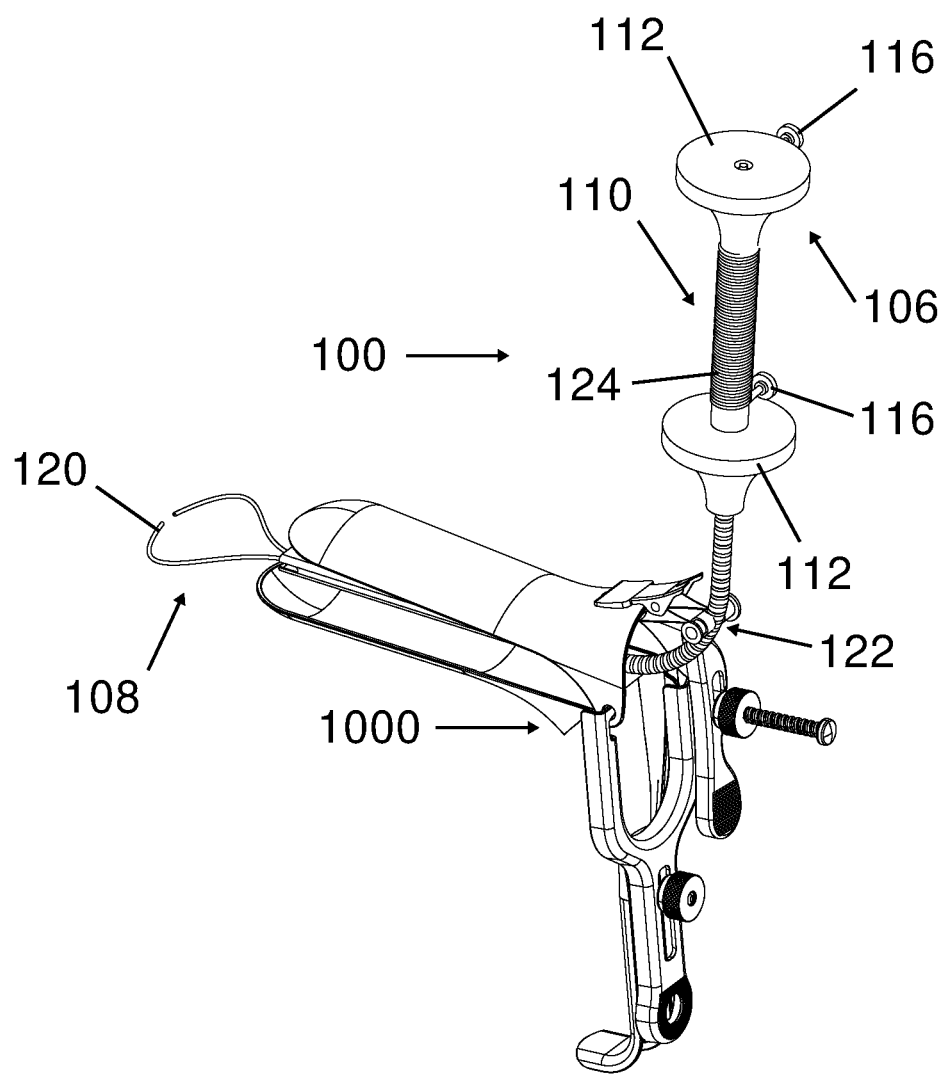
FIG. 10 is a perspective view of a cervical tenaculum device and anchor in use with a speculum, in accordance with an embodiment of the invention.

FIG. 10 is a perspective view of a cervical tenaculum device and anchor in use with a speculum, in accordance with an embodiment of the invention.

In some embodiments, the device 100 comprises a shaft 102 (sometimes called the interior shaft) comprised of a first end 104 and a second end 106; a clamp 108 configured to be locked or unlocked attached to the first end 104 of the shaft; an actuator shaft 110 that is removably coupled to the shaft 102, slidable along the shaft 102, and configured to open and close the clamp 108. In some embodiments, the invention has two or more handles 112 that can be attached along the length of the actuator shaft 110 or shaft 102; in some of these embodiments the portion of the actuator shaft 110 that is between the handles 112 may be comprised of a removably attached coil 124 such that when the handles 112 are pulled towards each other the interior shaft 102 is pressed forward, which operates the clamp 108 such as by opening it or altering its configuration.

Some configurations of the device 100 involve a shaft 102, with a clamp 108 attached at one end, enveloped by the actuator shaft 110 further comprised of a coil 124, with two handles 112 positioned such that one is at the end of the shaft opposite the clamp 108 and the other is at a roughly medial (though it may vary if needed) position along the shaft. The handle 112 near the end of the shaft 102 is attached to the shaft 102, while the handle 112 in the medial position is attached to the actuator shaft 110 at the end of the coil 124, such that when a user presses on the handle 112 at the end of the shaft 102 while holding the handle 112 located at the medial position it pushes the clamp 108 through the actuator shaft 110 and compresses the coil 124 of the actuator shaft 110, which in turn pushes the clamp 108 out of the sheath 118 as depicted in FIG. 8. When the pressure is released, the coil 124 of the actuator shaft 110 extends and the sheath 118 closes the clamp 108.

In some embodiments the device 100 is further comprised of an actuator shaft 110 that may be operated by a twisting movement, push-pull movement, plunger, quick-release screw, or other means of engaging the actuator and in turn the clamp 108. In some embodiments the actuator shaft 110 may have multiple components allowing it to be held in various configurations such as being configured to remove the actuator shaft 110 or portions thereof once the clamp 108 is in place, remove the actuator shaft 110 and shaft 102 entirely once the clamp 108 is in place, or leave the entire device 100 in the patient. In some embodiments, the actuator shaft 110 may further comprise a compressible coil 124 that may be removably attached to the actuator shaft 110 or held on to it by a handle 112 or set screw 116.

In some embodiments, the device 100 is comprised of an internal shaft 102 with at least two ends 104, 106. At one end the clamp 108 may be attached. An external shaft 110, the actuator shaft 110, may envelop the internal shaft 102; in which case it may be a hollow cylindrical shape so that it wraps around the internal shaft 102. The interior or actuator shafts 102, 110 may be at least partially flexible and/or compressible; in some embodiments the actuator shaft 110 may be further comprised of a removably attached coil 124 of material such as, but not limited to, metal or a polymer that may partially envelop the actuator shaft 110. In some embodiments, there may be two handles 112 attached at either end of the actuator shaft 110 in order to attach it to the internal shaft 102; and in some of those embodiments the handles 112 may be attached by screwing onto the internal shaft 102 to keep the external actuator shaft 110 in place, or may be attached by a set-screw 116, clasp, or clamp; in some embodiments the actuator shaft 110 or a portion thereof may be trapped between them or held via pressure from set screws 116 against the interior shaft 102. In some embodiments the clamp 108 is expressed and opened by pressing on the rear handle 112 so that the actuator shaft 110 compresses and in turn pushes the internal shaft 102 forward.

In some embodiments the internal 102 and actuator shafts 110 may be flexible such that they can be bent, allowing a practitioner to attach them to an anchor 114 or other grounding point while also moving them out of the way so that the practitioner can work. In some embodiments, the device 100 may have specific points along the internal 102 and actuator shafts 110 where the bending occurs, while in other embodiments the full length of the shaft 102, 110 components may be flexible. The internal or actuator shafts 102, 110 may have threading in some embodiments that is configured to receive one or more handles 112; in other embodiments the handles 112 attach via set-screws 116 that place press the handle into the shaft. The shafts may be substantially cylindrical, flat, or other shapes. In at least one embodiment the shafts 102, 110 are substantially cylindrical and the interior shaft 102 is able to rotate within the actuator shaft 110, though in various embodiments there may be pressures preventing free rotation such as pressure applying the handle 112 to the shaft 102 via the set screw 116, or a close fit from the actuator shaft 110. In some embodiments the shafts 102, 110 are substantially straight, while in others one or both shafts 102 110 may be curved or bent to enable specialized manipulation of tissue or articles.

In some embodiments, a practitioner or user engages the device by pressing on the actuator shaft 110 while pulling back on the shaft 102 or a handle 112 on the shaft 102, which in turn causes the clamp 108 to open. Some examples involve a sheath 118 attached to the actuator shaft 110 and overlapping the clamp 108 that fully covers it when the actuator shaft 110 is not being utilized, but when a user presses the handles 112 together it pushes the clamp 108 out of the sheath 118 which allows the clamp 108 to open; in such embodiments the clamp 108 may favor an opened position instead of closed or may even be a single piece of material which was constructed in an open position. Some embodiments may include a coil 124 between the handles 112 and at least partially enveloping the actuator shaft 110 to apply an opening pressure. The tips 120 of the clamp 108 can then be applied to a cervix or other article to be held, and once it is in a location the practitioner deems appropriate the actuator shaft 110 and handle(s) 112 can be released, which relieves the pressure keeping the clamp 108 open and closes the clamp 108, thereby taking hold of the article. The device 100 is then free to remain in the patient and grasping the article while the practitioner works utilizing other tools.

In some embodiments the clamp 108 is a jawed-clamp or other configuration wherein the clamp 108 may automatically favor a closed position over an open one and exerts tension on the points or pressure exerting areas of the clamp's tips 120. Some examples may have a complex clamp 108 structure wherein the clamp 108 has multiple modes that can be operated through the actuator shaft 110 and/or handles 112; such as locking the clamp 108 in its current position by twisting a handle 112 at a certain point, or it may have a click-in mechanism allowing it to hold pressure that can be quickly released. In some embodiments, the clamp 108 has a mechanism such as a screw, ratchet, or other variable tension means to place tension on the grasping means. In some embodiments the clamp 108 may be constructed as a single component wherein a piece of material, possibly a metal, is split and forked so that two tines are created, then bent towards each other, leaving a gap between them as necessary for the user, such that when the tines are pressed towards each other the tips 120 close the gap. In some embodiments, the tips 120 may contact each other, while in other embodiments they may overlap or pass each other. In some embodiments the mechanism is in the form of pointed tips 120 such as found in a common surgical tenaculum, or may be rounded, while in other embodiments it may involve a shaped pad or rod allowing it to displace the force over the surface it is grasping and diminish any trauma to the area or article being grasped. In some embodiments the clamp 108 may be a tether that encircles the area to be held like a noose or similar means. In some embodiments the clamp 108 is a pinch-based grasping means with two prongs, while in others it may have additional prongs as needed to sufficiently grasp and hold the article in question. In some embodiments, the clamp 108 is comprised of one or more hinges pivoted together such that when tension is placed on corresponding ends of the hinges the opposite ends are closed. In some embodiments, the clamp 108 is comprised of one or more hinges, such as scissor-hinges, that are connected with each other and operable against each other such that operating one hinge will operate another. In some embodiments the clamp 108 may be locked into position such that it does not exert any additional pressure once they are locked or closed to a certain degree; in other embodiments they may exert continuous closing or opening pressure. In some embodiment the clamp 108 may be at least partially flexible.

In some embodiments, the clamp 108 does not automatically favor a closed position but may favor a neutral or open position. Examples of such may feature a clamp 108 that is comprised of a single piece of material or it may have a spring integrated into the jaws of the clamp 108 that pushes it open. In some embodiments, the clamp 108 is also a scissors-style hinge mechanism wherein a distal end is designed to be a grasping end while a proximal end is the end engaged by the actuator shaft 110. In some embodiments, the clamp 108 may have a quick-release mechanism, retrieval cord, or other means of disengaging tension. In some embodiments, the scissors-style hinge clamp 108 may have a means of disengaging tension including a latch, catch, screw, and/or may be pushed on by the tether in order to release the tension.

In some embodiments the entire device 100 is disposable, while in others it is designed to be reused. In some embodiments certain components are disposable while other components in the same embodiment may be reusable. In some embodiments, the components of the device 100 may be comprised of one or more substances from the list including, but not limited to, silicone, plastic, metal, composites, or combinations thereof.

In some embodiments, the device 100 is further comprised of an anchor 114 that is comprised of a securing mechanism configured to be attached to a speculum 1000 or other surgical instrument or may be configured to adhere to skin or other surfaces and may be configured to hold the shafts 102, 110 or tether. The securing mechanism may be, but is not limited to, a mechanical clip, an adhesive patch, a pin, a needle to thread through a medium, a screw, an aperture 122 through which the shafts 102, 110 of the device 100 can be threaded (or said aperture 122 can be opened to allow the shaft to be threaded) and/or a clasp. The securing mechanism may alternatively be a combination of the aforementioned components configured in a complementary way. For some examples of the device 100, the anchor 114 includes a thread, hole, notch, clasp, or other means to secure the shaft or tether to the anchor 114, allowing the anchor 114 to hold tension on the shaft 102, 110 or tether and by extension the article that the clasp is holding. In some embodiments, the anchor 114 is configured to attach to a range of other surgical stabilizers or instruments including, but not limited to, a speculum 1000. For some embodiments, the anchor 114 is comprised in part of two overlapping cylinders wherein the two may be pushed together to expose and open an aperture 122 into which the device 100 or a portion thereof such as the shafts 102, 110 may be inserted.

In some embodiments the device 100 may be configured to integrate with other tools for a variety of purposes, such as integrating with a gynecological speculum to reduce the tenaculum's profile and further improve the visibility through the speculum.

Figure 11:
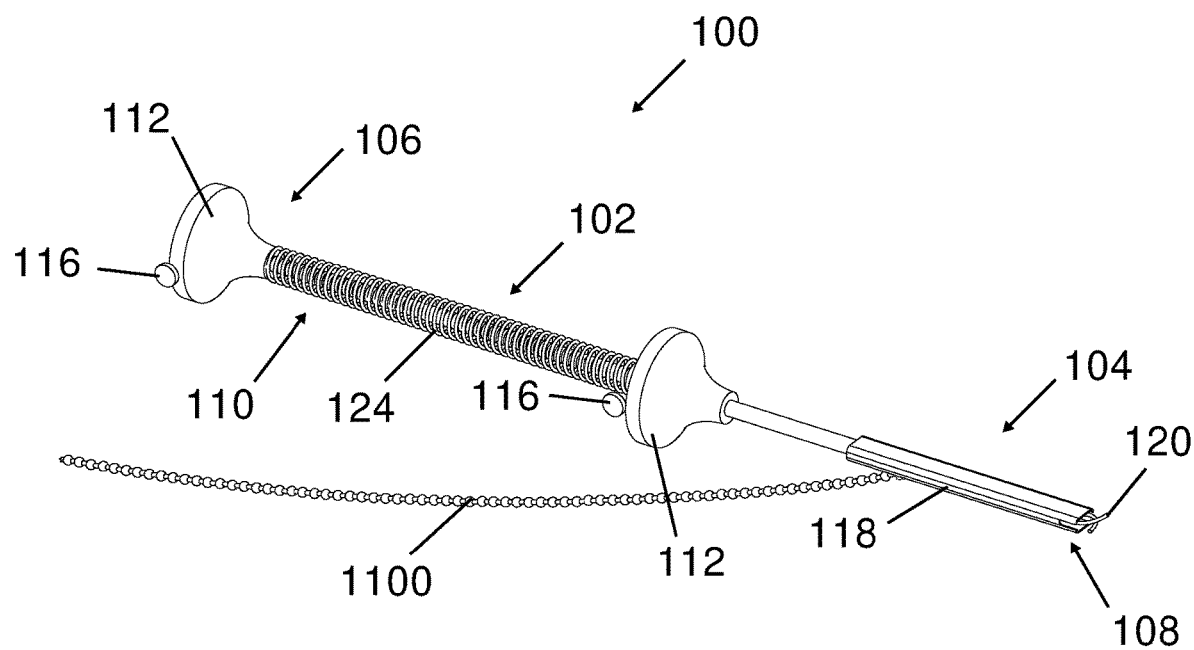
FIG. 11 is a perspective view of a cervical tenaculum device with tether, in accordance with an embodiment of the invention.

FIG. 11 is a perspective view of a cervical tenaculum device, in accordance with an embodiment of the invention.

In some embodiments, the device 100 comprises a shaft 102 (sometimes called the interior shaft) comprised of a first end 104 and a second end 106; a clamp 108 configured to be locked or unlocked attached to the first end 104 of the shaft; an actuator shaft 110 that is removably coupled to the shaft 102, slidable along the shaft 102, and configured to open and close the clamp 108. In some embodiments, the invention has two or more handles 112 that can be attached along the length of the actuator shaft 110 or shaft 102; in some of these embodiments the portion of the actuator shaft 110 that is between the handles 112 may be comprised of a removably attached coil 124 such that when the handles 112 are pulled towards each other the interior shaft 102 is pressed forward, which operates the clamp 108 such as by opening it or altering its configuration.

Some configurations of the device 100 involve a shaft 102, with a clamp 108 attached at one end, enveloped by the actuator shaft 110 further comprised of a coil 124, with two handles 112 positioned such that one is at the end of the shaft opposite the clamp 108 and the other is at a roughly medial (though it may vary if needed) position along the shaft. The handle 112 near the end of the shaft 102 is attached to the shaft 102, while the handle 112 in the medial position is attached to the actuator shaft 110 at the end of the coil 124, such that when a user presses on the handle 112 at the end of the shaft 102 while holding the handle 112 located at the medial position it pushes the clamp 108 through the actuator shaft 110 and compresses the coil 124 of the actuator shaft 110, which in turn pushes the clamp 108 out of the sheath 118. When the pressure is released, the coil 124 of the actuator shaft 110 extends and the sheath 118 closes the clamp 108.

In some embodiments the device 100 is further comprised of an actuator shaft 110 that may be operated by a twisting movement, push-pull movement, plunger, quick-release screw, or other means of engaging the actuator and in turn the clamp 108. In some embodiments the actuator shaft 110 may have multiple components allowing it to be held in various configurations such as being configured to remove the actuator shaft 110 or portions thereof once the clamp 108 is in place, remove the actuator shaft 110 and shaft 102 entirely once the clamp 108 is in place, or leave the entire device 100 in the patient. In some embodiments, the actuator shaft 110 may further comprise a compressible coil 124 that may be removably attached to the actuator shaft 110 or held on to it by a handle 112 or set screw 116.

In some embodiments, the device 100 is comprised of an internal shaft 102 with at least two ends 104, 106. At one end the clamp 108 may be attached. An external shaft 110, the actuator shaft 110, may envelop the internal shaft 102; in which case it may be a hollow cylindrical shape so that it wraps around the internal shaft 102. The interior or actuator shafts 102, 110 may be at least partially flexible and/or compressible; in some embodiments the actuator shaft 110 may be further comprised of a removably attached coil 124 of material such as, but not limited to, metal or a polymer that may partially envelop the actuator shaft 110. In some embodiments, there may be two handles 112 attached at either end of the actuator shaft 110 in order to attach it to the internal shaft 102; and in some of those embodiments the handles 112 may be attached by screwing onto the internal shaft 102 to keep the external actuator shaft 110 in place, or may be attached by a set-screw 116, clasp, or clamp; in some embodiments the actuator shaft 110 or a portion thereof may be trapped between them or held via pressure from set screws 116 against the interior shaft 102. In some embodiments the clamp 108 is expressed and opened by pressing on the rear handle 112 so that the actuator shaft 110 compresses and in turn pushes the internal shaft 102 forward.

In some embodiments the internal 102 and actuator shafts 110 may be flexible such that they can be bent, allowing a practitioner to attach them to an anchor 114 or other grounding point while also moving them out of the way so that the practitioner can work. In some embodiments, the device 100 may have specific points along the internal 102 and actuator shafts 110 where the bending occurs, while in other embodiments the full length of the shaft 102, 110 components may be flexible. The internal or actuator shafts 102, 110 may have threading in some embodiments that is configured to receive one or more handles 112; in other embodiments the handles 112 attach via set-screws 116 that place press the handle into the shaft. The shafts may be substantially cylindrical, flat, or other shapes. In at least one embodiment the shafts 102, 110 are substantially cylindrical and the interior shaft 102 is able to rotate within the actuator shaft 110, though in various embodiments there may be pressures preventing free rotation such as pressure applying the handle 112 to the shaft 102 via the set screw 116, or a close fit from the actuator shaft 110. In some embodiments the shafts 102, 110 are substantially straight, while in others one or both shafts 102 110 may be curved or bent to enable specialized manipulation of tissue or articles.

In some embodiments, a practitioner or user engages the device by pressing on the actuator shaft 110 while pulling back on the shaft 102 or a handle 112 on the shaft 102, which in turn causes the clamp 108 to open. Some examples involve a sheath 118 attached to the actuator shaft 110 and overlapping the clamp 108 that fully covers it when the actuator shaft 110 is not being utilized, but when a user presses the handles 112 together it pushes the clamp 108 out of the sheath 118 which allows the clamp 108 to open; in such embodiments the clamp 108 may favor an opened position instead of closed or may even be a single piece of material which was constructed in an open position. Some embodiments may include a coil 124 between the handles 112 and at least partially enveloping the actuator shaft 110 to apply an opening pressure. The tips 120 of the clamp 108 can then be applied to a cervix or other article to be held, and once it is in a location the practitioner deems appropriate the actuator shaft 110 and handle(s) 112 can be released, which relieves the pressure keeping the clamp 108 open and closes the clamp 108, thereby taking hold of the article. The device 100 is then free to remain in the patient and grasping the article while the practitioner works utilizing other tools.

In some embodiments the clamp 108 is a jawed-clamp or other configuration wherein the clamp 108 may automatically favor a closed position over an open one and exerts tension on the points or pressure exerting areas of the clamp's tips 120. Some examples may have a complex clamp 108 structure wherein the clamp 108 has multiple modes that can be operated through the actuator shaft 110 and/or handles 112; such as locking the clamp 108 in its current position by twisting a handle 112 at a certain point, or it may have a click-in mechanism allowing it to hold pressure that can be quickly released. In some embodiments, the clamp 108 has a mechanism such as a screw, ratchet, or other variable tension means to place tension on the grasping means. In some embodiments the clamp 108 may be constructed as a single component wherein a piece of material, possibly a metal, is split and forked so that two tines are created, then bent towards each other, leaving a gap between them as necessary for the user, such that when the tines are pressed towards each other the tips 120 close the gap. In some embodiments, the tips 120 may contact each other, while in other embodiments they may overlap or pass each other. In some embodiments the mechanism is in the form of pointed tips 120 such as found in a common surgical tenaculum, or may be rounded, while in other embodiments it may involve a shaped pad or rod allowing it to displace the force over the surface it is grasping and diminish any trauma to the area or article being grasped. In some embodiments the clamp 108 may be a tether that encircles the area to be held like a noose or similar means. In some embodiments the clamp 108 is a pinch-based grasping means with two prongs, while in others it may have additional prongs as needed to sufficiently grasp and hold the article in question. In some embodiments, the clamp 108 is comprised of one or more hinges pivoted together such that when tension is placed on corresponding ends of the hinges the opposite ends are closed. In some embodiments, the clamp 108 is comprised of one or more hinges, such as scissor-hinges, that are connected with each other and operable against each other such that operating one hinge will operate another. In some embodiments the clamp 108 may be locked into position such that it does not exert any additional pressure once they are locked or closed to a certain degree; in other embodiments they may exert continuous closing or opening pressure. In some embodiment the clamp 108 may be at least partially flexible.

In some embodiments, the clamp 108 does not automatically favor a closed position but may favor a neutral or open position. Examples of such may feature a clamp 108 that is comprised of a single piece of material or it may have a spring integrated into the jaws of the clamp 108 that pushes it open. In some embodiments, the clamp 108 is also a scissors-style hinge mechanism wherein a distal end is designed to be a grasping end while a proximal end is the end engaged by the actuator shaft 110. In some embodiments, the clamp 108 may have a quick-release mechanism, retrieval cord, or other means of disengaging tension. In some embodiments, the scissors-style hinge clamp 108 may have a means of disengaging tension including a latch, catch, screw, and/or may be pushed on by the tether in order to release the tension.

In some embodiments the device 100 further comprises a tether 1100 that may be attached along the length of the device. In some embodiments this tether 1100 is comprised of silicone or another substance from the list including, but not limited to, silicone, rubber or plastic. In some embodiments, the tether 1100 is a chain made of one or more substances from the list including, but not limited to, metal or plastic. In some embodiments, the tether 1100 can be pulled to place tension on the clamp 108 and allow a user to in turn place tension on the article which the clamp 108 is grasping, such as, but not limited to, in the case of gynecological procedures, a cervix. In some embodiments the clamp 108 is attached to the tether by a variable tension means such as, but not limited to, a spring. In some embodiments, the tether 1100 is comprised of a chain from the list including, but not limited to, a box chain or a ball chain. The tether 1100 may, in some examples, be attached loosely to the device via a ring that is smaller than the handles 112 and thus trapped between them, or it may be smaller than a handle 112 and the near end of a sheath 118 for the clamp, also trapping it between them.

In some embodiments the entire device 100 is disposable, while in others it is designed to be reused. In some embodiments certain components are disposable while other components in the same embodiment may be reusable. In some embodiments, the components of the device 100 may be comprised of one or more substances from the list including, but not limited to, silicone, plastic, metal, composites, or combinations thereof.

In some embodiments, the device 100 is further comprised of an anchor 114 that is comprised of a securing mechanism configured to be attached to a speculum or other surgical instrument or may be configured to adhere to skin or other surfaces and may be configured to hold the shafts 102, 110 or tether 1100. The securing mechanism may be, but is not limited to, a mechanical clip, an adhesive patch, a pin, a needle to thread through a medium, a screw, an aperture through which the shafts 102, 110 of the device 100 can be threaded (or said aperture can be opened to allow the shaft to be threaded) and/or a clasp. The securing mechanism may alternatively be a combination of the aforementioned components configured in a complementary way. For some examples of the device 100, the anchor 114 includes a thread, hole, notch, clasp, or other means to secure the shaft or tether 1100 to the anchor 114, allowing the anchor 114 to hold tension on the shaft 102, 110 or tether 1100 and by extension the article that the clasp is holding. In some embodiments, the anchor 114 is configured to attach to a range of other surgical stabilizers or instruments including, but not limited to, a speculum. For some embodiments, the anchor 114 is comprised in part of two overlapping cylinders wherein the two may be pushed together to expose and open an aperture into which the device 100 or a portion thereof such as the shafts 102, 110 may be inserted.

In some embodiments the device 100 may be configured to integrate with other tools for a variety of purposes, such as integrating with a gynecological speculum to reduce the tenaculum's profile and further improve the visibility through the speculum.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

In some instances, one or more components may be referred to herein as "configured to," "configured by," "configurable to," "operable/operative to," "adapted/adaptable," "able to," "conformable/conformed to," etc. Those skilled in the art will recognize that such terms (e.g. "configured to") generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects. It will be understood by those within the art that, in general, terms used herein, are generally intended as "open" terms (e.g., the term "including" should be interpreted as "including but not limited to," the term "having" should be interpreted as "having at least," the term "includes" should be interpreted as "includes but is not limited to," etc.).

Accordingly, the scope of the invention is not limited by the disclosure of these preferred and alternate embodiments. Instead, the invention should be determined by reference to the claims that follow.

What is claimed is:

1. A surgical device comprising:
    a shaft comprised of a first end and a second end;
    a clamp configured to be locked or unlocked that is attached to the first end of the shaft; and
    an actuator shaft that is removably coupled to the shaft, slidable along the shaft, and configured to open and close the clamp; and
    a tether which is removably coupled to the first end of the shaft and configured to apply tension to the clamp.

2. The device of claim 1, wherein the shaft is at least partially flexible at one or more points along its length, and the actuator shaft is at least partially flexible at one or more points along its length.

3. The device of claim 1, wherein the clamp is comprised of one or more prongs.

4. The device of claim 3, wherein a number of prongs is two.

5. The device of claim 3, wherein the one or more prongs end in a tip that curves inwards towards a medial longitudinal axis of the device.

6. The device of claim 3, wherein the clamp further comprises a housing that the one or more prongs at least partially withdraw into when the actuator shaft is not engaged.

7. The device of claim 3, wherein the clamp is in a closed position when the actuator shaft is not engaged.

8. The device of claim 1, wherein the device further comprises one or more locking handles configured to attach to the shaft and to prevent the actuator shaft from sliding off of the shaft.

9. The device of claim 1, wherein the actuator shaft is at least partially comprised of a coil.

10. The device of claim 9, wherein the actuator shaft is configured to lock when twisted.

11. The device of claim 1, wherein the actuator shaft is further comprised of a segment that is removably coupled to the shaft and is at least partially flexible.

12. The device of claim 1, wherein the device is further comprised of an anchor.

13. The device of claim 12, wherein the anchor is removably coupled to the shaft.

14. The device of claim 13, wherein the anchor is comprised of a secondary clamp.

15. The device of claim 13, wherein the anchor coupled to the shaft by inserting the shaft into an aperture in the anchor.

16. The device of claim 15, wherein the shaft is at least partially flexible.

17. The device of claim 16, wherein the aperture in the anchor is configured to direct the shaft at least partially away from a center line of the device.

18. The device of claim 1, wherein the shaft is rigid along at least a part of its length and flexible along at least another part.

19. The device of claim 1, wherein the actuator shaft is further comprised of two handles wherein one handle is removably coupled to a proximal end of the actuator shaft and the second handles is removably coupled to a distal end of the actuator shaft.

20. A surgical device comprising:
    an interior shaft wherein at least a portion of the shaft is flexible, and the interior shaft is comprised of a first end and a second end wherein the second end of the interior shaft is threaded;
    a clamp configured to be locked or unlocked attached to the first end and comprised of two prongs that are coupled at a pivot point; a tether which is removably coupled to the first end of the shaft and configured to apply tension to the clamp;

two or more shaft locking handles; and an actuator shaft removably coupled to the shaft and configured to slide over at least part of the shaft and open and close the clamp when the actuator shaft is pressed towards the clamp, wherein the actuator shaft is coupled to the shaft by sliding a first shaft locking handle over the interior shaft, then the actuator shaft over the interior shaft, and then a second shaft locking handle behind the actuator shaft so that the first shaft locking handles prevent the actuator shaft from sliding off of the interior shaft in either direction.

\* \* \* \* \*